(12) United States Patent
Zhang et al.

(10) Patent No.: US 11,554,016 B2
(45) Date of Patent: *Jan. 17, 2023

(54) ARTIFICIAL CHORDAE TENDINEAE IMPLANTATION SYSTEM

(71) Applicant: HANGZHOU VALGEN MEDTECH CO., LTD., Zhejiang (CN)

(72) Inventors: Tingchao Zhang, Zhejiang (CN);
Weiwei Zhang, Zhejiang (CN);
Chunyuan Zhou, Zhejiang (CN)

(73) Assignee: HANGZHOU VALGEN MEDTECH CO., LTD., Zhejiang (CN)

( * ) Notice: Subject to any disclaimer, the term of this patent is extended or adjusted under 35 U.S.C. 154(b) by 372 days.

This patent is subject to a terminal disclaimer.

(21) Appl. No.: 16/749,337

(22) Filed: Jan. 22, 2020

(65) Prior Publication Data

US 2020/0155313 A1 May 21, 2020

Related U.S. Application Data

(63) Continuation of application No. PCT/CN2018/100507, filed on Aug. 14, 2018.

(30) Foreign Application Priority Data

Nov. 7, 2017 (CN) .......................... 201711084957.9

(51) Int. Cl.
*A61F 2/24* (2006.01)
*A61B 17/34* (2006.01)
(Continued)

(52) U.S. Cl.
CPC .............. *A61F 2/2457* (2013.01); *A61B 5/06* (2013.01); *A61B 17/3468* (2013.01);
(Continued)

(58) Field of Classification Search
CPC .................................. A61F 2/24; A61F 2/2457
See application file for complete search history.

(56) References Cited

U.S. PATENT DOCUMENTS

| | | | |
|---|---|---|---|
| 2004/0044365 A1 | 3/2004 | Bachman | |
| 2005/0021056 A1 | 1/2005 | St. Goar et al. | |

(Continued)

FOREIGN PATENT DOCUMENTS

| | | |
|---|---|---|
| CN | 101495049 A | 7/2009 |
| CN | 101902975 A | 12/2010 |

(Continued)

OTHER PUBLICATIONS

The Extended European Search Report issued in corresponding EP Application No. EP18876471.6, dated Jul. 27, 2021.

(Continued)

*Primary Examiner* — Vi X Nguyen
(74) *Attorney, Agent, or Firm* — Hauptman Ham, LLP

(57) ABSTRACT

An artificial chordae tendineae implantation system includes a clamping device, a puncture device, a pushing device, and a detection device. The pushing device includes a pushing shaft. The clamping device includes a clamping push rod that receives an artificial chorda tendineae, and a distal clamp and a proximal clamp for cooperatively clamping a valve leaflet. The detection device includes one probe that is movably disposed in the pushing shaft. A probe outlet is provided at one of a clamping surface of the proximal clamp and a clamping surface of the distal clamp, and a probe accommodation chamber corresponding to the probe outlet is provided at the other one. When the clamping device is closed, the distal end of the probe protrudes from the probe outlet and is accommodated in the probe accommodation chamber, and whether the valve leaflet is clamped is detected.

21 Claims, 14 Drawing Sheets

(51) Int. Cl.
    *A61B 5/06*    (2006.01)
    *A61F 2/30*    (2006.01)
    *A61F 2/46*    (2006.01)
    *A61B 17/00*   (2006.01)

(52) U.S. Cl.
    CPC .. *A61F 2/2466* (2013.01); *A61B 2017/00243* (2013.01); *A61B 2017/00862* (2013.01); *A61B 2017/3425* (2013.01); *A61B 2017/3445* (2013.01); *A61B 2017/3488* (2013.01); *A61F 2002/3008* (2013.01); *A61F 2002/4622* (2013.01)

(56) References Cited

U.S. PATENT DOCUMENTS

2005/0165419 A1* 7/2005 Sauer .................. A61B 1/0014
                                                        606/148
2006/0069304 A1* 3/2006 Takemoto .......... A61B 1/00087
                                                        600/104
2007/0049952 A1  3/2007 Weiss
2009/0105729 A1  4/2009 Zentgraf
2012/0022633 A1  1/2012 Olson et al.

FOREIGN PATENT DOCUMENTS

| | | |
|---|---|---|
| CN | 104055600 A | 9/2014 |
| CN | 104248457 A | 12/2014 |
| CN | 108186163 A | 6/2018 |
| WO | 2008112237 A3 | 9/2008 |
| WO | 2017066888 A1 | 4/2017 |

OTHER PUBLICATIONS

International Search Report relating to International Application No. PCT/CN2018/100507 dated Nov. 1, 2018.

* cited by examiner

ARTIFICIAL CHORDAE TENDINEAE IMPLANTATION SYSTEM

CROSS-REFERENCE TO RELATED APPLICATIONS

This application is a continuation of International Application No. PCT/CN2018/100507 filed on Aug. 14, 2018, which claims priority to Chinese Patent Application No. CN201711084957.9 filed on Nov. 11, 2017, the contents each of which are incorporated by reference in their entirety.

TECHNICAL FIELD

The present disclosure relates to the technical field of medical devices, and relates to a device for repairing heart valve defects, in particular to an artificial chordae tendineae implantation system.

BACKGROUND

The mitral valve is a one-way "valve" between the left atrium (LA) and the left ventricle (LV), which ensures that blood flows from the left atrium to the left ventricle. Referring to FIG. 1, a normal healthy mitral valve has multiple chordae tendineae. The leaflets of the mitral valve are divided into an anterior leaflet and a posterior leaflet. When the left ventricle is in a diastolic state, the two leaflets are in an open state, and the blood flows from the left atrium to the left ventricle; when the left ventricle is in a contracted state, the chordae tendineae are stretched to ensure that the leaflets will not be rushed into the left atrium by the blood flow, and the anterior and posterior leaflets are well closed, thereby ensuring that the blood flows from the left ventricle through the aortic valve (AV) to the aorta. If there is a lesion in the chordae tendineae or papillary muscles, such as a rupture of the chordae tendineae of the posterior leaflet as shown in FIG. 2, when the left ventricle is in a contracted state, the mitral valve cannot return to a closed state as normal, and the impulse of the blood flow will further cause the leaflet to be detached into the left atrium, causing blood reflux.

At present, lesions in the chordae tendineae are treated by surgically implanting artificial chordae tendineae. This requires adopting invasive open thoracotomy approaches, under general anesthesia, and moderate hypothermic cardiopulmonary bypass as auxiliary support. Such surgical operations have the disadvantages of complicated surgical procedures, high surgical costs, high degrees of patient trauma, high risks of complications, long hospitalization, and painful recovery processes.

At present, there is a device that implants artificial chordae tendineae by minimally invasive open surgery approaches. The device first clamps a leaflet by a capturing device, and then determines the clamping effect by a capturing verification system, and then implants the artificial chordae tendineae. The operational principle of the capturing verification system is making a determination by using an optical fiber to generate different colors upon meeting the leaflet and the blood. When the leaflet is clamped, an optical fiber transmits to the leaflet clamping surface of the capturing device and generates optical signals like reflection and refraction, and another optical fiber detects the signals to determine whether the leaflet is clamped. The artificial chordae tendineae implanting device applies the optical fibers to the interventional therapy device, resulting in a complicated device structure. Also, the optical fibers must enter a patient's body with the device, thereby increasing the surgical risks. In addition, since the capturing verification system must be equipped with capturing verification monitors, the device structure becomes more cumbersome, the manufacturing process is complicated, and the production cost and the operation cost are high.

SUMMARY

In response to the disadvantages of the prior art, the present disclosure provides an artificial chordae tendineae implantation system that accurately and efficiently determines the state of the clamping of the leaflet.

The present disclosure provides an artificial chordae tendineae implantation system, including a clamping device, a puncture device, a pushing device, and a detection device. The pushing device includes a pushing shaft. The clamping device includes a clamping push rod that receives at least an artificial chorda tendinea, a distal clamp and a proximal clamp for cooperatively clamping a leaflet. The distal clamp is disposed at a distal end of the clamping push rod. The proximal clamp is disposed at a distal end of the pushing shaft. The puncture device and the clamping push rod are movably insertedly mounted within the pushing shaft respectively. The detection device includes at least a probe, and the probe is movably insertedly mounted within the pushing shaft. A probe outlet is provided at one of a clamping surface of the proximal clamp and a clamping surface of the distal clamp, and a probe accommodation chamber corresponding to the probe outlet is provided at the other one of the clamping surfaces of the proximal clamp and the clamping surface of the distal clamp. When the distal clamp closes with the proximal clamp, a distal end of the probe protrudes from the probe outlet and is received in the probe accommodation chamber.

The artificial chordae tendineae implantation system of the present disclosure has beneficial technical effects in light of the prior art:

The artificial chordae tendineae implantation system of the present disclosure allows the proximal clamp to be closed with the distal clamp when the leaflet is not clamped or the position of clamping deviates, and the distal end of the probe can be pushed out of the probe outlet and into the probe accommodation chamber. When the leaflet is clamped, the leaflet covers the probe outlet, the probe cannot smoothly enter into the probe accommodation chamber, so the clamping effect of the leaflet is verified, thereby accurately and efficiently verifying the clamping effect of the leaflet, preventing a usage of monitoring devices such as optical fibers and optical monitors. The artificial chordae tendineae implantation system of the present disclosure has a simple structure, is easy to operate, lowers the surgical risks, has a low manufacturing cost, and lowers a patient's economic burden.

BRIEF DESCRIPTION OF THE DRAWINGS

To illustrate the present disclosure more clearly, the accompanying drawings and embodiments are introduced in the following.

DETAILED DESCRIPTION OF THE EMBODIMENTS

The present disclosure will be described in details in combination with the accompanying drawings and embodiments such that the purpose, technical solution and advantages of the present disclosure will be more apparent. It should be understood that the particular embodiments are described for the purpose of illustrating as opposed to restricting the present disclosure.

For the sake of facilitation of illustrating, a position near the operator is defined as a proximal end, and a position away from the operator is defined as a distal end.

The First Embodiment

Figure 12:
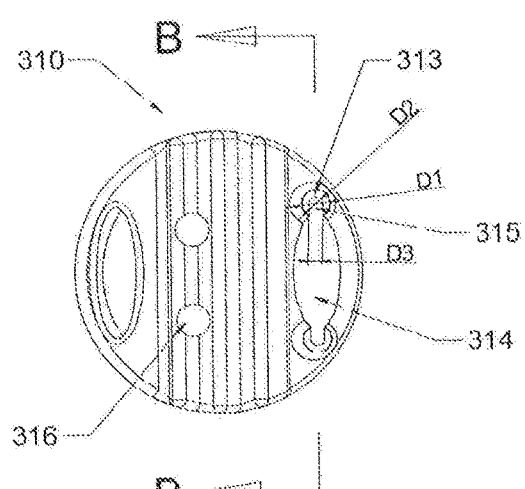
FIG. 12 is a structural schematic diagram of the clamping surface of the distal clamp of the artificial chordae tendineae implantation system according to the first embodiment.
Figure 13:
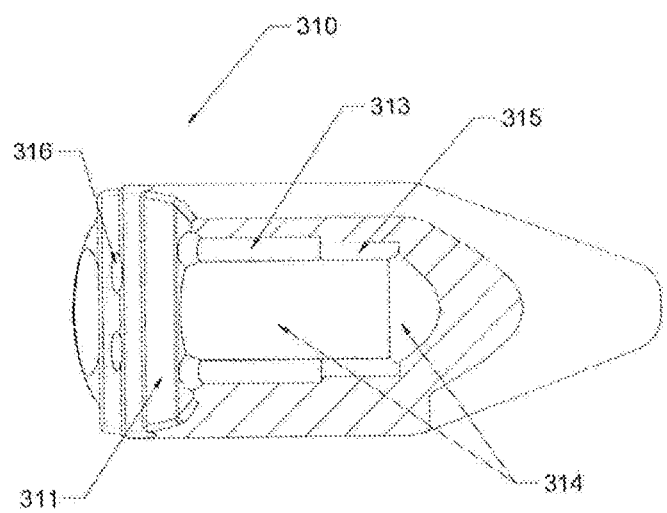
FIG. 13 is a cross-sectional view along the line B-B of FIG. 12.

Referring to FIG. 3 to FIG. 36, the artificial chordae tendineae implantation system of the present disclosure is used for implanting sutures into a patient's body as artificial chordae tendineae, to replace the chordae tendineae having a lesion or a rupture in the patient's heart. The artificial chordae tendineae implantation system includes a clamping device 300, a puncture device 400, a pushing device 200, and a detection device 600. The pushing device 200 includes a pushing shaft 210. The puncture device 400 includes two puncture push rods 420 and two puncture needles 410 that are disposed at the distal ends of the two puncture push rods 420 respectively. The clamping device 300 includes a clamping push rod 330 for receiving an artificial chorda tendinea 100, and a distal clamp 310 and a proximal clamp 320 for cooperatively clamping a leaflet. The distal clamp 310 is disposed at a distal end of the clamping push rod 330. The proximal clamp 320 is disposed at a distal end of the pushing shaft 210. The puncture device 400 and the clamping push rod 330 are movably insertedly mounted within the pushing shaft 210 respectively. The detection device 600 includes at least a probe 610, the probe 610 is movably insertedly mounted within the pushing shaft 210. As shown in FIG. 23, the clamping surface of the proximal clamp 320 is provided with a probe outlet 321. As shown in FIG. 9, FIG. 12, and FIG. 13, the clamping surface of the corresponding distal clamp 310 is provide with a probe accommodation chamber 316 that corresponds to the probe outlet 321 and is used for receiving the distal end of the probe 610. When the proximal clamp 320 closes with the distal clamp 310, the distal end of the probe 610 passes through the probe outlet 321 and is received in the probe accommodation chamber 316. As such, when there is no leaflet between the proximal clamp 320 and the distal clamp 310, the proximal clamp 320 and the distal clamp 310 can be completely closed, and the distal end of the probe 610 can be pushed into the probe accommodation chamber 316. After the pushing shaft 210 is inserted into the chest of a patient, and after a leaflet is clamped by way of the distal clamp 310 and the proximal clamp 320 of the clamping device 300, if the distal end of the probe 610 may be pushed into the probe accommodation chamber 316, then it indicates that the probe 610 is not stopped by the leaflet, the leaflet is not clamped or there is a deviation in the clamping position, the clamping effect is not ideal, thereby requiring a modification of the position of the artificial chordae tendineae implantation system to clamp the leaflet again; if the distal end of the probe 610 cannot be pushed into the probe accommodation chamber 316, it indicates that the probe 610 is stopped by the leaflet, the clamping effect of the leaflet is good, and the operator may perform leaflet puncturing and implant the artificial chorda tendinea 100.

Referring to FIG. 4 to FIG. 7, the artificial chorda tendinea 100 includes a flexible chorda tendinea main body 110. The chorda tendinea main body 110 is used to be implanted into a heart to replace a natural chorda tendinea with a lesion. The chorda tendinea main body 110 has a first end and a second end respectively. The first end and/or the second end are connected to a fixing member 120. The fixing member 120 is used for a detachable or non-detachable connection with the puncture needle 410 of the puncture device 400.

One end of the chorda tendinea main body 110 is fixed on the leaflet, and the other end can be fixed on the ventricular wall or the papillary muscle to replace the natural chorda tendinea with a lesion, thereby maintaining the tension between the leaflet and the ventricular wall or the papillary muscle. A flexible chorda tendinea main body 110 means that it can bend freely in the axial direction without stretching. Generally, the chorda tendinea main body 110 is in the form of a flexible wire. The material of the chorda tendinea main body 110 may be a polymer material compatible with a human body or a relatively soft metal material, particularly a polymer material.

Figure 4:
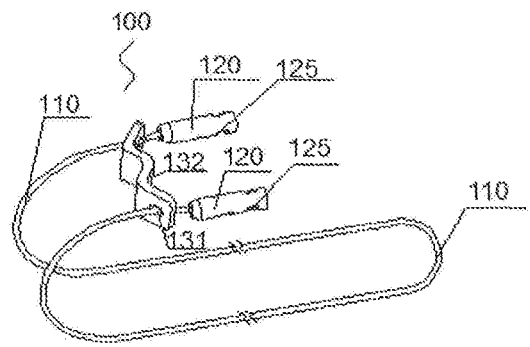
FIG. 4 is a structural schematic diagram of the artificial chordae tendineae of the artificial chordae tendineae implantation system according to the first implementation manner of the first embodiment.
Figure 5:
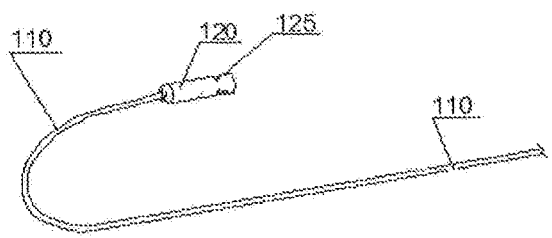
FIG. 5 is a structural schematic diagram of the artificial chordae tendineae according to the second implementation manner.
Figure 7:
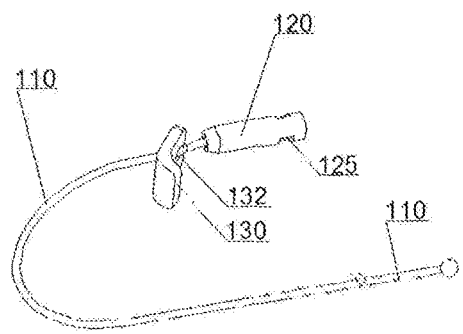
FIG. 7 is a structural schematic diagram of the artificial chordae tendineae according to the fourth implementation manner.

Referring to FIG. 4, the fixing member 120 may be disposed at both ends of the chorda tendinea main body 110, or may be disposed at one end of the chorda tendinea main body 110 as shown in FIG. 5. The artificial chordae tendineae implantation system may be provided with a single artificial chorda tendinea 100, two or more artificial chordae tendineae 100 (as shown in the drawings). The chorda tendinea main body 110 may be connected with the fixing member 120 by tying, winding, welding, bonding, snap fitting, or the like. For example, one end of the chorda tendinea main body 110 may pass through the fixing member 120 and then is tied to form a larger diameter coil, or the end may be welded to form a larger diameter ball, or the end may be provided with a positioning rod. In a natural state, the positioning rod has a different axis from the chorda tendinea main body 110 and the fixing member 120. After the positioning rod and one end of the chorda tendinea main body 110 pass through the fixing member 120, the positioning rod returns to the natural state and snap blocks at the back side of the fixing member 120, thereby fixing one end of the chorda tendinea main body 110 to the fixing member 120. As shown in FIG. 7, when the first end of the chorda tendinea main body 110 is provided with the fixing member 120, and the second end of the chorda tendinea main body 110 is not provided with the fixing member 120, the second end of the chorda tendinea main body 110 may, by way of tying, winding, or providing a spherical end, a disc-shaped end, or the like, have a cross-sectional dimension of the second end of the chorda tendinea main body 110 greater than a cross-sectional dimension of the chorda tendinea main body 110, thereby blocking the second end of the chorda tendinea main body 110 on the upper surface of the leaflet. In this embodiment, the number of the artificial chorda tendinea 100 is one, and the fixing member 120 is disposed at the first end and the second of the chorda tendinea main body 110 (as shown in FIG. 4).

The shape of the fixing member 120 corresponds to different connection manners. The outer portion of the fixing member 120 is generally cylindrical, and the cross-sectional shape may be various shapes such as a circle, an ellipse, a polygon, etc., particularly a circular shape or an elliptical shape.

There are various ways of connecting the fixing member 120 to the puncture needle 410, such as a threaded connection, a bond, a rough surface friction connection, an interference fit, or a snap connection. In this embodiment, a snap connection is adopted. Specifically, the inner surface of the fixing member 120 is provided with an indentation or a hole, and the puncture needle 410 is correspondingly provided with a protrusion or a protruding edge snap fit, and the fixing member 120 forms a non-detachable or detachable connection with the puncture needle 410.

Figure 8:
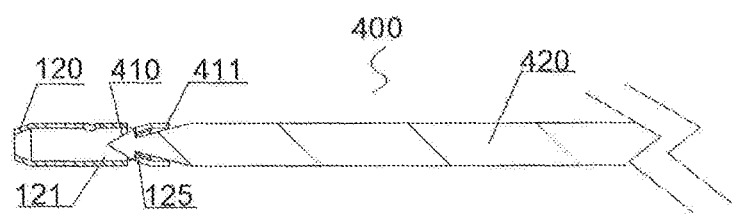
FIG. 8 is a structural schematic diagram of a connection between the fixing member and the puncture needle of the artificial chordae tendineae implantation system according to the first embodiment.
Figure 9:
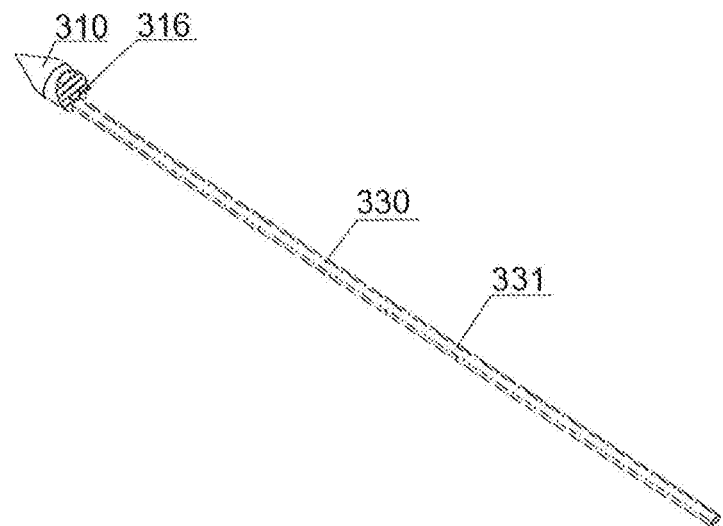
FIG. 9 is a structural schematic diagram of the clamping push rod and the distal clamp of the artificial chordae tendineae implantation system according to the first embodiment.

Referring to FIG. 8, a receiving chamber 121 is disposed in the axial direction of the fixing member 120. The inner wall of the receiving chamber 121 is provided with three recesses 125 in the radial direction, and the puncture needle 410 is correspondingly provided with a protruding edge 411 to be snap fit with the recesses 125. The number of the recesses 125 is set to three, which not only ensures the stability of the connection between the fixing member 120 and the puncture needle 410, so as to reduce the amplitude of the pulsation of the puncture needle 410 after the connecting, but also avoids increasing the diameter of the puncture needle 410.

Referring to FIG. 4 to FIG. 7, for the purpose of converting point contact into face contact between the artificial chorda tendinea 100 and the leaflet, so as to effectively reduce the risk of tearing the leaflet by the artificial chorda tendinea 100, particularly an anti-slip member 130 is sleeved on the chorda tendinea main body 110, and the anti-slip member 130 can slide in an axial direction along the chorda tendinea main body 110. Since the anti-slip member 130 is pre-installed on the chorda tendinea main body 110, after the puncture needle 410 punctures the leaflet and is connected to the chorda tendinea main body 110, the anti-slip member 130 can be driven to the puncturing point and fixed on the leaflet together with the chorda tendinea main body 110. The anti-slip member 130 is set on the artificial chorda tendinea 100 as follows:

Referring to FIG. 4, in accordance with one implementation manner, the anti-slip member 130 is provided with at least two through holes 131, and the first end and the second end of the chorda tendinea main body 110 respectively pass through different through holes 131 and then are connected with the fixing member 120 respectively.

Figure 6:
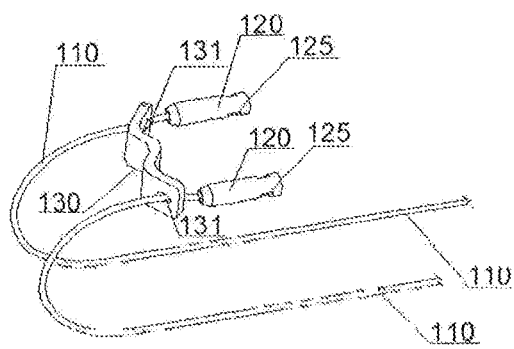
FIG. 6 is a structural schematic diagram of the artificial chordae tendineae according to the third implementation manner.

Referring to FIG. 6, in accordance with another implementation manner, the anti-slip member 130 is provided with at least two through holes 131, and multiple chorda tendinea main bodies 110 respectively pass through different through holes 131, meaning multiple chorda tendinea main bodies 110 share a common anti-slip member 130.

Referring to FIG. 7, in accordance with another implementation manner, the chorda tendinea main body 110 is provided with an anti-slip member 130, and the anti-slip member 130 is provided with a through hole 131. The first end of the chorda tendinea main body 110 passes through the through hole 131 and then is connected with the fixing member 120. The second end of the chorda tendinea main body 110 is not provided with the fixing member 120. The second end, by way of tying or providing a spherical end, a disc-shaped end, or the like, has a cross-sectional dimension of the second end greater than a cross-sectional dimension of the through hole 131 of the anti-slip member 130.

In this embodiment, the anti-slip member 130 is provided with two through holes 131, the first end and the second end of the chorda tendinea main body 110 pass through one of the through holes 131 respectively and then are connected with a fixing member 120 respectively.

In order to disperse the force of the chorda tendinea main body 110 on the leaflet as far as possible to the contact surface between the anti-slip member 130 and the leaflet, the anti-slip member 130 needs to fit the leaflet as much as possible, so the anti-slip member 130 is provided with a fitting surface 132 that fits the leaflet. Except the fitting surface 132, the anti-slip member 130 is not restricted to a specific structure, and may have multiple structures: for example it may be a sheet having a certain area, a disc shape or a spherical shape, or even an irregular shape, particularly a sheet shape. The anti-slip member 130 may be a non-porous structure, a mesh structure, a bar-like structure, or the like. The anti-slip member 130 is made of a biocompatible material, may be made of an elastic material or a non-elastic material. Specifically, the anti-slip member 130 is selected from at least one of an elastic spacer, a patch, a felt sheet, a mesh structure, a disc-like structure, or a double disc-like structure. The disc-like structure or the double disc-like structure of the anti-slip member 130 is similar to an occluder in the prior art, and the details will not be repeated herein. Particularly, in order to reduce the overall size of the devices, the anti-slip member 130 having a disc-like structure or a double disc-like structure is made of a shape memory material.

Figure 1:
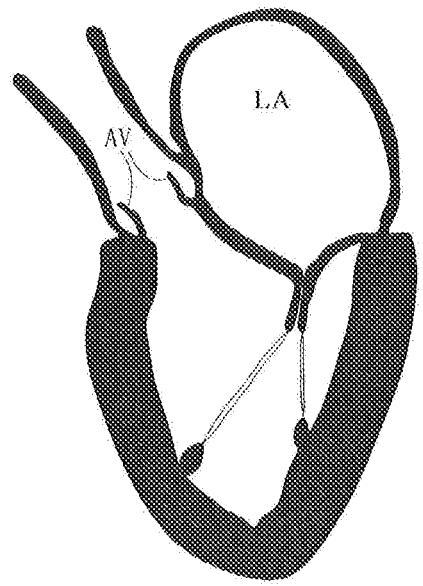
FIG. 1 is a schematic diagram illustrating normal chordae tendineae in a heart.
Figure 2:
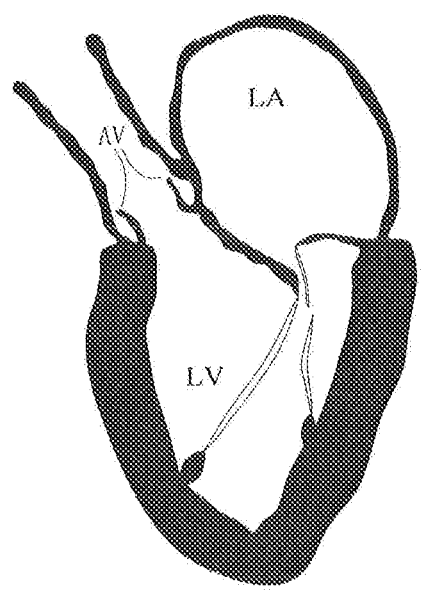
FIG. 2 is a schematic diagram illustrating ruptured chordae tendineae in a heart.
Figure 3:
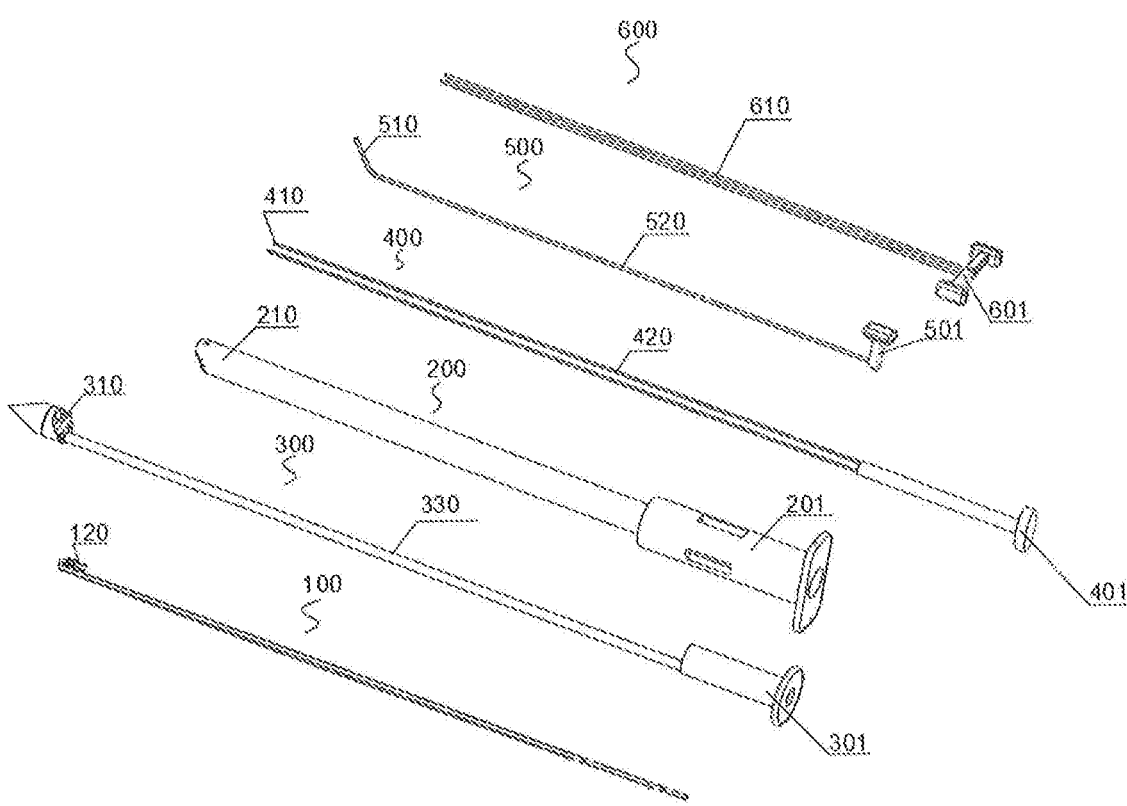
FIG. 3 is an exploded view of an artificial chordae tendineae implantation system having a detection device according to the first embodiment of the present disclosure.

Referring to FIG. 3, the pushing shaft 210 of the pushing device 200 has a tubular body having a certain axial length or a rod having an inner chamber. The pushing shaft 210 particularly is provided with a plurality of mutually separated through inner chambers in the axial direction. The pushing shaft 210 may be an integrally formed multi-chambers tube, or the outer tube and the inner tube may be sleeved and secured together to form the pushing shaft 210 in a unitary structure. The pushing shaft 210 may be made of a biocompatible polymer material, for example, polyoxymethylene (POM), polyethylene (PE), nylon (PA), polyvinyl chloride (PVC), acrylonitrile-butadiene-styrene copolymer (ABS), nylon elastomer (Pebax) or Polyurethane (PU), or a metal material, for example, stainless steel or nickel titanium alloy, or a metal-polymer composite material. The proximal end of the pushing shaft 210 is provided with the first handle 201 for operating the pushing shaft 210 to push towards the distal end or retracts to the proximal end.

Referring to both FIG. 3 and FIG. 8, the puncture needle 410, after puncturing the leaflet, may be connected with the fixing member 120 of the artificial chorda tendinea 100, so as to pull the chorda tendinea main body 110 towards the proximal end. The distal end of the puncture needle 410 is a conical straight tip, so as to facilitate the puncturing of the leaflet and reduce the diameter of the puncturing point formed on the leaflet. Techniques in the prior art use a needle having a hook-shaped head to penetrate a leaflet, take sutures that are used as artificial chordae tendineae, then pull back the needle to drive the artificial chordae tendineae to pass through the leaflet, then fix one end of the artificial chordae tendineae on the ventricular wall. This type of needle having a hook-shaped head forms a relatively large puncturing point on the leaflet, causing severe damage to the leaflet, not only affecting the recovery process of the patient after the surgery, but also increasing the risk of tearing the leaflet after the surgery. In contrast, a conical straight tip causes a small puncturing point on the leaflet, beneficial to the recovering process for the patient after the surgery. The artificial chordae tendineae implantation system of this embodiment forms a single puncturing point on each leaflet having a diameter ranging from 0.3 mm to 1.5 mm. Further, by selecting a suitable shape and diameter of the puncture needle 410, the diameter of the puncturing point can be limited to about 0.7 mm.

The distal end of the puncture needle 410 is provided with at least a protruding tooth or at least a protruding edge for forming an interference fit or a snap connection with the fixing member 120. It is understood that, in other implementation manners, the puncture needle 410 may form a non-detachable or detachable connection with the fixing member 120 of the artificial chorda tendinea 100 by a threaded connection, a bond, a friction connection, or the like. The puncture push rod 420 is movably insertedly mounted within the inner chamber of the pushing shaft 210. The proximal end of the puncture push rod 420 passes through from the proximal end of the pushing shaft 210 and is connected with the third handle 401. Through the axial movement of the third handle 401, the puncture push rod 420 is driven to move along the axial direction of the pushing shaft 210, so as to drive the puncture needle 410 to puncture towards the distal end or to retract to the proximal end. After the leaflet is clamped by the clamping device 300, the puncture needle 410 may be driven by the third handle 401 to penetrate the leaflet and is connected with the fixing member 120 of the artificial chorda tendinea 100. The puncture needle 410 and the artificial chorda tendinea 100 are connected by the fixing member 120 as a whole. The needle having a hook-shaped head in the prior art has a smaller possibility of taking the artificial chordae tendineae, causing a low success rate of surgery and a prolonged surgical time; and after the needle takes the artificial chordae tendineae, since the needle and the artificial chordae tendineae are connected only by weak frictional force, during the process of retracting the needle, due to the blood flushing of the patient or the movement by the operator, the artificial chordae tendineae are easily detached from the needle, resulting in a failure of the surgery and a prolonged surgical time. But in this embodiment, the puncture needle 410 and the chorda tendinea main body 110 of the artificial chorda tendinea 100 form a stable indirect connection by way of the fixing member 120, causing it difficult for the artificial chorda tendinea 100 to be detached from the puncture needle 410, so the operator may conveniently and quickly pull one end or two ends of the artificial chorda tendinea 100 connected with the fixing member 120 to a predetermined position of the ventricular wall or the papillary muscle.

Figure 10:
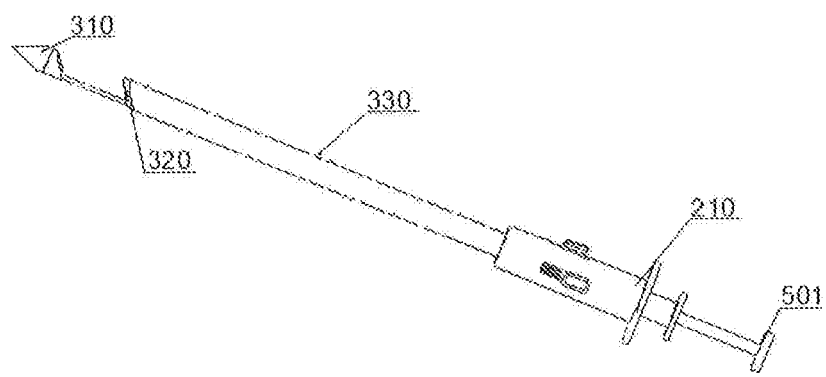
FIG. 10 is a structural schematic diagram of the clamping device in an open state of the artificial chordae tendineae implantation system according to the first embodiment.
Figure 11:
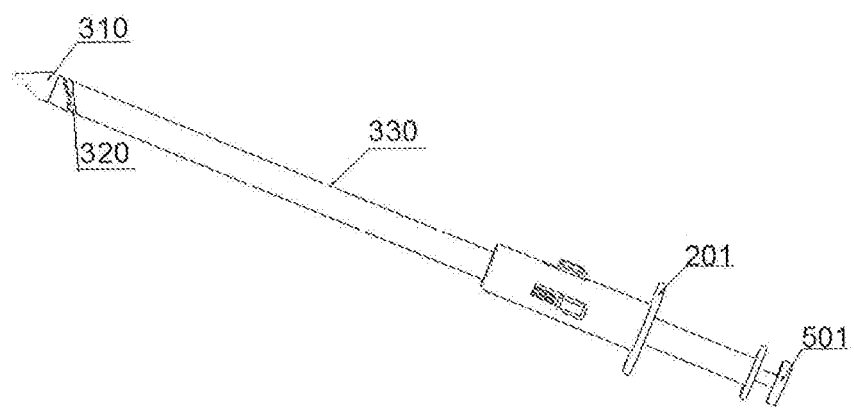
FIG. 11 is a structural schematic diagram of the clamping device in a closed state of the artificial chordae tendineae implantation system according to the first embodiment.

Referring to FIG. 3 and FIG. 9 to FIG. 11, the proximal end of the clamping push rod 330 of the clamping device 300 passes through from the proximal end of the pushing shaft 210 and is provided with the second handle 301. As such, by pushing the second handle 310 towards the distal end, the clamping push rod 330 is driven to move towards the distal end, causing the distal clamp 310 to move away from the proximal clamp 320, resulting in an open state of the clamping device 300, as shown in FIG. 10, and a leaflet accommodation space is formed between the distal clamp 310 and the proximal clamp 320. The distal end of the device is fine adjusted to cause the leaflet to enter into the leaflet accommodation space, then the second handle 301 is retracted towards the proximal end, the clamping push rod 330 is driven to move towards the proximal end, making the distal clamp 310 to move closer to the proximal clamp 320, resulting in a closed state of the clamping device 300, as shown in FIG. 11. At this time, the leaflet is clamped by the clamping device 300 and fixed. The shapes of the proximal clamp 320 and the distal clamp 310 should be consistent with the shape of the pushing shaft 210, and the distal clamp 310 and the proximal clamp 320 should form a smooth overall after the closing to facilitate the pushing and reducing the damage to the patient's wound. It is understood that, afore-mentioned state of pushing the second handle 301 towards the distal end to make the distal clamp 310 move away from the proximal clamp 320, may also be achieved by retracting the first handle 201 and the pushing shaft 210 towards the proximal end; the state of retracting the second handle 301 towards the proximal end to make the distal clamp 310 to move closer to the proximal clamp 320, may also be achieved by pushing the first handle 201 and the pushing shaft 210 towards the distal end.

It is understood that, in other embodiments, there is no need to separately provide a proximal clamp 320, and the distal end of the pushing shaft 210 is directly used as the proximal clamp 320 to cooperates with the distal clamp 310 to clamp the leaflet. In this implementation manner, the pushing shaft 210 particularly has a rod-shaped body having a plurality of separated inner chambers, the distal surface of the rod-shaped body serving as a clamping surface of the leaflet.

To improve the stability of the clamping, the clamping surface of the proximal clamp 320 (i.e., the distal surface of the proximal clamp 320) and the clamping surface of the distal clamp 310 (i.e., the proximal surface of the distal clamp 310) are supposed to be mutually fitting, and have a large leaflet contact area respectively. For example, the two clamping surfaces can be tilted separately, i.e., both having an acute angle less than 90 degrees with respect to the axis of the pushing shaft 210. Also, the clamping surface(s) of the distal clamp 310 and/or the proximal clamp 320 is provided with a clamping reinforcement member for reinforcing the clamping force. The clamping reinforcement member is particularly at least one of a protrusion, a rib, an indentation or a pit. And the shape of the clamping reinforcement member provided at the clamping surface of the distal clamp 310 is supposed to mutually fit the shape of the clamping reinforcement member provided at the clamping surface of the proximal clamp 320, so as to leave no gap between the closed distal clamp 310 and the proximal clamp 320. In this embodiment, the clamping surface of the distal clamp 310 and the clamping surface of the proximal clamp 320 are respectively provided with a plurality of parallel ribs used as the clamping reinforcement members. When the clamping device 300 is closed, there is no gap between the distal clamp 310 and the proximal clamp 320.

Referring to FIG. 9, FIG. 12, and FIG. 13, the clamping push rod 330 is a tubular body or a hollow rod-shaped body having a certain axial length, and the cross section is particularly elliptical or circular, and the clamping push rod 330 is provided with an artificial chorda tendinea channel 331 along the axial direction. The distal clamp 310 is provided with two artificial chordae tendineae accommodation chambers 315 that are connected with the artificial chorda tendinea channel 331. The two artificial chordae tendineae accommodation chambers 315 respectively are connected through with the clamping surface of the distal clamp 310. The chorda tendinea main body 110 of the artificial chorda tendinea 100 is received in the artificial chorda tendinea channel 331 and the artificial chordae tendineae accommodation chambers 315.

The clamping surface of the distal clamp 310 is provided with two fixing chambers 313 that are used to receive two fixing members 120 of the artificial chorda tendinea 100 respectively. Each fixing chamber 313 is axially connected with an artificial chordae tendineae accommodation chamber 315. The positions of the two fixing chambers 313 correspond respectively to the positions of the two puncture needles 410. As such, the two fixing members 120 of the artificial chorda tendinea 100 are received respectively in the distal clamp 310, and the proximal end of each fixing member 120 corresponds to a puncture needle 410.

The prior art techniques expose the artificial chordae tendineae to outside the artificial chordae tendineae implantation system, causing the outer surface of the artificial chordae tendineae implantation system to be not smooth, thereby causing the frictional damage to the tissues and blood leakage during the artificial chordae tendineae implantation system entering the human body, increasing the risk of postoperative complications. This embodiment disposes and fixes the artificial chorda tendinea 100 inside the artificial chordae tendineae implantation system, avoiding afore-mentioned problems. Also, in the prior art, the artificial chordae tendineae are implanted with a U-shaped loop combined with a hook-shaped needle, thereby causing wrinkles at the edge of the leaflet, causing the edge of the leaflet to form an artificial gap, which will not form a matching edge, making it easy to result in the mitral regurgitation and a non-ideal surgical result. The artificial chordae tendineae implantation system according to this embodiment has the distance between the fixing chamber 313 of the distal clamp 310 and the clamping push rod 330 as the distance between the artificial chorda tendinea 100 implanted in the heart and the edge of the leaflet, thereby effectively preventing the edge of the leaflet from folding and enhancing the surgical effect.

Since the artificial chorda tendinea 100 is provided with the anti-slip member 130, the clamping surface of the distal clamp 310 is provided with an accommodation indentation 314 for receiving the anti-slip member 130. The accommodation indentation 314 is in radial connection with the two artificial chordae tendineae accommodation chambers 315, respectively. As such, after the two puncture needles 410 respectively puncture the anterior leaflet and the posterior leaflet of the mitral valve and respectively connect with a fixing member 120, the two puncture push rods 420 may be retracted towards the proximal end respectively, driving the two puncture needles 410 and fixing members 120 that respectively connect with the two puncture needles 410, the chorda tendinea main body 110, and the anti-slip member 130 to be pulled out successively from the clamping surface of the distal clamp 310, till the puncture needle 410, the fixing members 120, and the chorda tendinea main body 110 pass the leaflet successively and the anti-slip member 130 fits the upper surface of the leaflet.

The fixing chamber 313 and the accommodation indentation 314 make it possible to pull the chorda tendinea main body 110 and the anti-slip member 130 to the leaflet without loosening the distal clamp 310 and the proximal clamp 320. As such, when the clamping device 300 changes from the closed state to the open state, at the moment when the leaflet is detached from the clamping device 300 and resume flapping, the chorda tendinea main body 110 does not contact the leaflet alone, thereby preventing damage to the flapping leaflet by the linear cutting effect of the chorda tendinea main body 110.

The fixing chamber 313 is used to secure the fixing member 120 of the artificial chorda tendinea 100 inside the fixing chamber 313, and is also used to pull the fixing member 120, after pulled by external forces, smoothly from the fixing chamber 313. As such, the shape of the fixing chamber 313 is supposed to correspond to the shape of the fixing member 120, and the diameter of the inscribed circle of the fixing chamber 313 is larger than the diameter of the circumcircle of the artificial chordae tendineae accommodation chamber 315. Particularly, the ratio of the diameter of the circumcircle of the artificial chordae tendineae accommodation chamber 315 to the diameter of the inscribed circle of the fixing chamber 313 is (0.2~0.4):1. When the cross sections of the fixing chamber 313 and the artificial chordae tendineae accommodation chamber 315 are both circular, the diameter of the inscribed circle of the fixing chamber 313 is the diameter of the circular cross section of the fixing chamber 313, and the diameter of the circumcircle of the artificial chordae tendineae accommodation chamber 315 is the diameter of the circular cross section of the artificial chordae tendineae accommodation chamber 315. In this embodiment, the fixing chamber 313 has a circular cross section with a diameter D1, the artificial chordae tendineae accommodation chamber 315 has a circular cross section with a diameter D2, and D2 is 30% of D1. The purpose of this configuration is: if D2 is too large, when the puncture needle 410, driven by the puncture push rod 420, is engaged with the fixing member 120 of the artificial chorda tendinea 100, due to the pushing force towards the distal end by the puncture push rod 420, the fixing member 120 may slip from the fixing chamber 313 into the artificial chordae tendineae accommodation chamber 315, and consequently the connection between the puncture needle 410 and the fixing member 120 of the artificial chorda tendinea 100 cannot be achieved in a one-time success, thereby prolonging the surgical time; if D2 is too small, the chorda tendinea main body 110 of the artificial chorda tendinea 100 cannot pass smoothly through the artificial chordae tendineae accommodation chamber 315, and consequently, after the connection between the puncture needle 410 and the fixing member 120 of the artificial chorda tendinea 100 is achieved, the artificial chorda tendinea 100 cannot be smoothly pulled out of the clamping surface of the clamping push rod 330. It is understood that, in other embodiments, the cross sections of the fixing chamber 313 and the artificial chordae tendineae accommodation chamber 315 can also be elliptical, triangular, quadrilateral, polygonal, and the like, as long as the shape of the fixing chamber 313 mutually fits the shape of the fixing member 120 and the shape of the artificial chordae tendineae accommodation chamber 315 does not affect the smooth passing through of the chorda tendinea main body 110 within the artificial chordae tendineae accommodation chamber 315.

In order to smoothly pull both the chorda tendinea main body 110 and the anti-slip member 130 out of the clamping surface of the distal clamp 310, the fixing chamber 313 is radially connected with the accommodation indentation 314. Particularly, a width D3 of the connected portion between the fixing chamber 313 and the accommodation indentation 314 is 20%-50% of D1. The purpose of this configuration is: if D3 is too large, the fixing member 120 of the artificial chorda tendinea 100 cannot be firmly secured in the fixing chamber 313 of the distal clamp 310, and is easy to slip from the fixing chamber 313, causing malfunctioning of the devices; if D3 is too small, after the puncture needle 410 is connected with the fixing member 120 of the artificial chorda tendinea 100, the fixing member 120 cannot be smoothly pulled out of the fixing chamber 313, causing a surgical failure.

Figure 14:
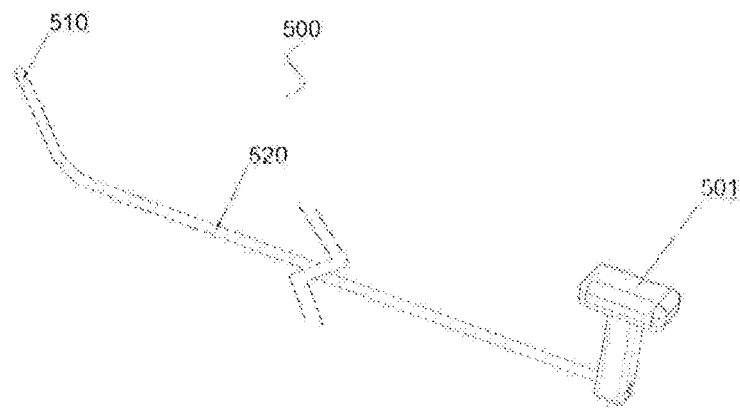
FIG. 14 is a structural schematic diagram of the clamping assistance device of the artificial chordae tendineae implantation system according to the first implementation manner of the first embodiment.

Referring to FIG. 14, to further improving the clamping, the artificial chordae tendineae implantation system is also provided with a clamping assistance device 500. The clamping assistance device 500 includes a clamping assistance arm 520 that is movably insertedly mounted within the pushing shaft 210, and a clamping assistance member 510 disposed at the distal end of the clamping assistance arm 520. To facilitate the pushing, the proximal end of the clamping assistance arm 520 is provided with the fourth handle 501.

Figure 15:
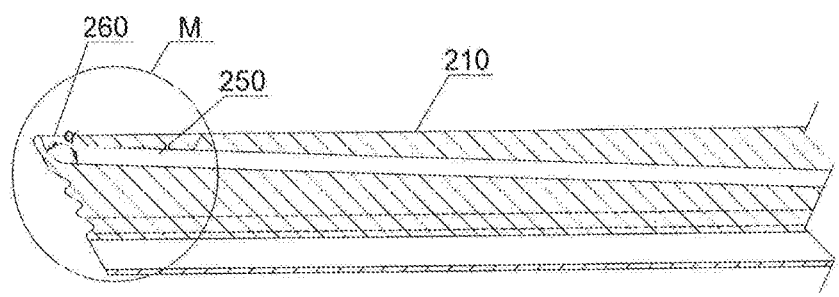
FIG. 15 is an axial cross-sectional view of the pushing shaft of the artificial chordae tendineae implantation system according to the first implementation manner of the first embodiment.
Figure 16:
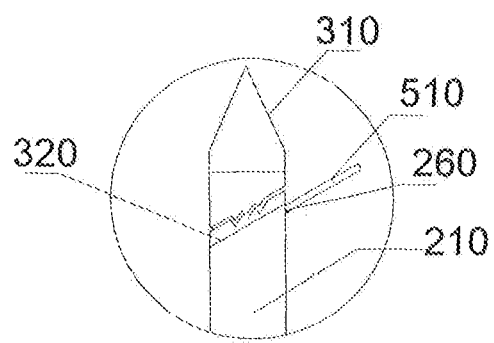
FIG. 16 is a structural schematic diagram of the clamping assistance arm pushing the clamping assistance member as shown in FIG. 14.
Figure 17:
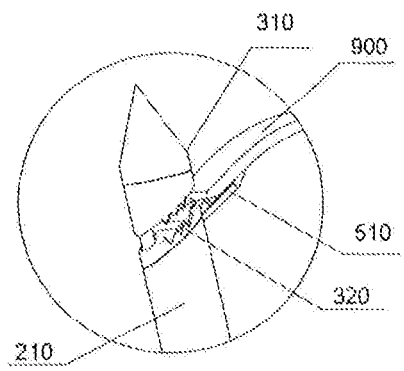
FIG. 17 is a structural schematic diagram of the clamping assistance member supporting a leaflet as shown in FIG. 14.

Referring to FIG. 15, the pushing shaft 210 is axially provided with an assistance arm accommodation chamber 250. Before the puncturing, both the clamping assistance member 510 and the clamping assistance arm 520 are received in the assistance arm accommodation chamber 250. The clamping surface of the proximal clamp 320, the side wall of the pushing shaft 210, or the side wall of the proximal clamp 320 are provided with an opening 260. The opening 260 is through connected with the assistance arm accommodation chamber 250. When the operator pushes the fourth handle 501 towards the distal end, the clamping assistance arm 520 may be driven to push the clamping assistance member 510 to pass through the opening 260 (as shown in FIG. 16), thereby supporting the lower surface of the leaflet, stabilizing the flapping leaflet, reducing the amplitude of movement of the leaflet, cooperating with the clamping device 300 to clamp and secure the leaflet (as shown in FIG. 17).

Referring to FIG. 15, the first implementation manner of the assistance arm accommodation chamber 250 is: the assistance arm accommodation chamber 250 has a generally straight chamber body, the entire assistance arm accommodation chamber 250 is disposed obliquely in the pushing shaft 210, and an angle α between the axis of the distal end of the assistance arm accommodation chamber 250 and the axis of the pushing shaft 210 ranges from 120° to 150°. The purpose of this configuration is: before the puncturing, the clamping push rod 330 contacts the edge of the leaflet, the distal clamp 310 and the proximal clamp 320 can only clamp part of the leaflet. In order to keep the flapping leaflet stable as much as possible to facilitate the puncturing, it is necessary to provide a supporting force on the other side opposite to the edge of each leaflet. Consequently, a certain angle between the clamping assistance member 510 and the pushing shaft 210 is required, so as to support the lower surface of the other side opposite to the leaflet edge of each leaflet. The angle between the clamping assistance member 510 and the pushing shaft 210 is approximately equal to the angle α between the axis of the distal end of the assistance arm accommodation chamber 250 and the axis of the pushing shaft 210.

Figure 18:
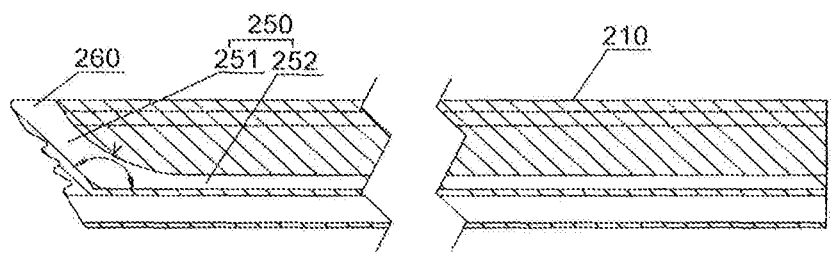
FIG. 18 is an axial cross-sectional view of the distal end of the pushing shaft according to the second implementation manner.

Referring to FIG. 18, the second implementation manner of the assistance arm accommodation chamber 250 is: the assistance arm accommodation chamber 250 includes a distal chamber body 251 and a proximal chamber body 252. The proximal chamber body 252 is substantially parallel to the axial direction of the pushing shaft 210, and the angle γ between the distal chamber body 251 and the proximal chamber body 252 ranges from 120° to 150°. As long as a smooth transition between the distal chamber body 251 and the proximal chamber body 252 is ensured, without affecting that the clamping assistance arm 520 passes smoothly in the assistance arm accommodation chamber 250.

Referring again to FIG. 14 and FIG. 17, the clamping assistance member 510 supports the lower surface of the leaflet 900 and cooperates with the clamping device 300 to clamp the leaflet. The clamping assistance member 510 is made of an elastic and/or flexible material to accommodate the anatomical structure of the leaflet and the amplitude of movement of the leaflet, and to avoid damage to the leaflet. The elastic material is particularly a shape memory material. The clamping assistance member 510 may be made of a metal material, a polymer material, or a metal-polymer composite material.

In this embodiment, the clamping assistance member 510 is a support rod. The support rod may be a solid or hollow structure having a single-layer or a multi-layer composite structure, or may be wound from a single wire or a plurality of wires. The cross section of the support rod may be a regular circular or elliptical shape, a crescent shape, a semicircular shape, a polygonal shape, or the like. The clamping assistance member 510 has a smooth shape, and the distal end is formed by laser spot welding to form a smooth round head without defects such as burrs, edges or corners. In this embodiment, the clamping assistance member 510 is made of an elastic nickel-titanium alloy with a shape memory function and has a circular cross section.

The clamping assistance arm 520 is rod-shaped or tubular with a certain axial length, and has a certain hardness or rigidity to provide support and pushing abilities. The clamping assistance arm 520 may be made of a metal rod or a polymer rod with a solid or hollow structure having a single-layer or a multi-layer composite structure, or may be wound from a single wire or a plurality of wires. The cross section of the clamping assistance arm 520 may be a regular circular or elliptical shape, a crescent shape, a semicircular shape, a polygonal shape, or a circular shape. The clamping assistance arm 520 can be made of a metal material, a polymer material, or a metal-polymer composite. In this embodiment, the clamping assistance arm 520 is made of an elastic material with a memory function and has a circular cross section.

The support of the clamping assistance arm 520 and the softness of the clamping assistance member 510 can be achieved by using different materials respectively. That is, the clamping assistance arm 520 is made of a hard material; the clamping assistance member 510 is made of an elastic and/or flexible material. It is understood that, the clamping assistance arm 520 and the clamping assistance member 510 can also be made of the same material, and then a material having a higher hardness is added to the outside or inside of the clamping assistance arm 520 as a reinforcing tube or a stiffened wire to ensure the support of the clamping assistance arm 520.

The clamping assistance member 510 is made of a material opaque to X-rays. In the prior art, before the clamping device 300 clamps the leaflet, the relative position between the clamping device and the leaflet cannot be determined by methods such as X-rays that require a lower level of operation, and must rely on the accurate ultrasonography to move the clamping device to a suitable position, and the pulsating state of the leaflet is monitored by ultrasonography, the relative movement between the distal clamp and the proximal clamp is quickly driven to clamp the leaflet when the leaflet pulsates near the clamping device. Ultrasonography imposes a higher requirement on the operational techniques and analytical abilities of cardiac ultrasonography images of a doctor, causing an increased surgical cost, a higher surgical difficulty, and a prolonged surgical time. In this embodiment, the clamping assistance member 510 is made of a material opaque to X-rays, after the clamping assistance member 510 contacts the leaflet, the flexible and/or elastic clamping assistance member 510 generates corresponding oscillations accompanying the amplitude of the movement of the leaflet. As such, before the clamping device 300 clamps the leaflet, the operator may quickly and accurately determine the position of the leaflet by X-rays, so as to more quickly and accurately operate the clamping device 300 to clamp the leaflet, thereby reducing the surgical cost and difficulty, shortening the surgical time, and increasing the surgical success rate.

Figure 19A:
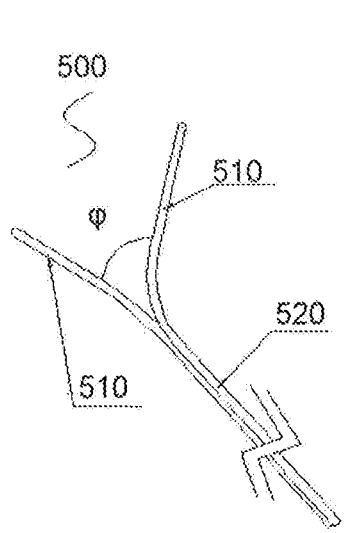
FIG. 19a and FIG. 19b are structural schematic diagrams of the clamping assistance device according to the second implementation manner and the third implementation manner.

It is understood that, in other embodiments, in order to enhance the strength of the clamping assistance device 500, the clamping assistance member 510 may also be a deformed structure composed of a plurality of support rods. The deformed structure is contracted and deformed and then received in the pushing shaft 210 together with the clamping assistance arm 520. As shown in FIG. 19a, the deformed structure is an open bifurcated structure or an umbrella structure composed of a plurality of support rods, and an angle φ between the bifurcated structures is less than or equal to 150°. In order to facilitate pushing in the pushing shaft 210, the clamping assistance member 510 has a compressed state and a stretched state in a natural state. The clamping assistance member 510 in the compressed state, can be received in the assistance arm accommodation chamber 250 of the pushing shaft 210 and pushed; when the clamping assistance member 510 passes through the opening 260 that is provided at the clamping surface of the proximal clamp 320, the side wall of the pushing shaft 210, or the side wall of the proximal clamp 320, converts to the stretched state, and may support the lower surface of the leaflet and stabilize the flapping leaflet. The contact surface of the clamping assistance member 510 with the leaflet is the plane where the clamping assistance member 510 is located. Therefore, the contact area between the clamping assistance device 500 and the leaflet is larger, thereby better fitting the leaflet, and improving the support to the leaflet by the clamping assistance device 500.

Figure 19B:
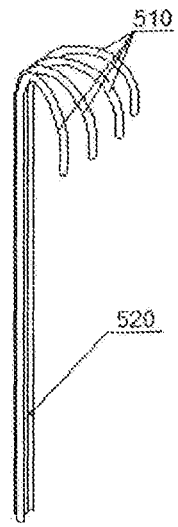

It is understood that, in other embodiments, the end of the clamping assistance member 510 in a bifurcated structure or an umbrella structure may roll towards the proximal end of the clamping assistance arm 520, and a plurality of clamping assistance members 510 form a recessed area, as shown in FIG. 19b. At this time, because the end of each clamping assistance member 510 rolls inwardly towards the proximal end of the clamping assistance arm 520, thereby preventing the support rod of the clamping assistance member 510 from stabbing the leaflet or the ventricular wall.

Figure 20A:
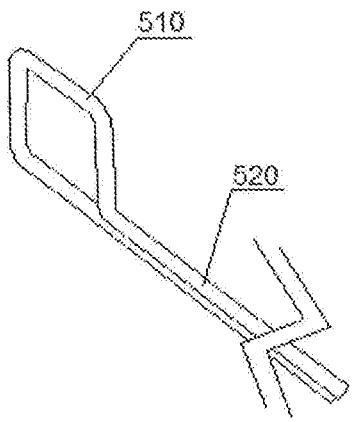
FIG. 20a to FIG. 20c are structural schematic diagrams of the clamping assistance device according to the fourth implementation manner to the sixth implementation manner.
Figure 20B:
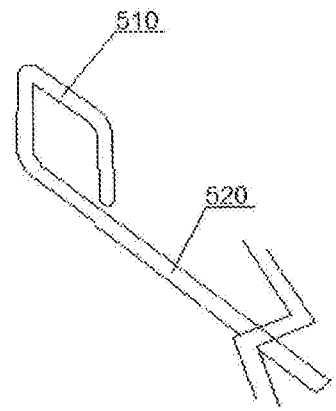
Figure 20C:
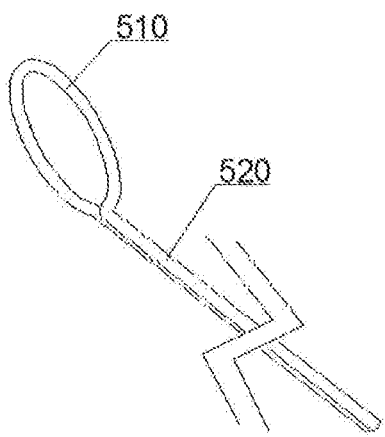

Referring to FIG. 20a to FIG. 20c, it is understood that, in other embodiments, the deformed structure may also be a closed loop structure composed of at least one support rod. The closed loop structure may be circular, diamond, elliptical, pear-shaped, polygonal or other irregular shape that may form a closed structure.

Figure 21:
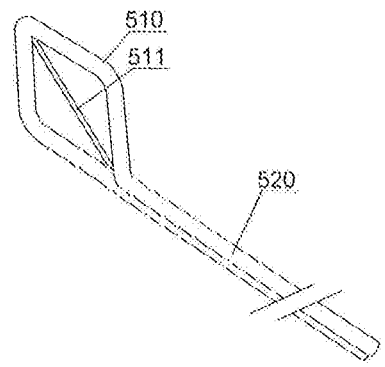
FIG. 21 is a structural schematic diagram of the clamping assistance device according to the seventh implementation manner.

Referring to FIG. 21, it is understood that, in other embodiments, at least one connecting rod 511 having flexibility and/or elasticity may be disposed between the support rods of the closed loop structure to improve the self-stability of the closed loop structure, and further enhance the supporting force of the clamping assistance member 510 on the leaflet.

It is understood that, in other embodiments, when a plurality of support rods and connecting rods are disposed in the closed loop structure, the closed loop structure may also form a sheet structure or a mesh structure. It can also be understood that, in other embodiments, the mesh structure may be heat-treated, such that the mesh structure may form a stretchable disc-shaped structure (similar to a single disc occluder in the prior art). The disc-shaped structure can be further heat-treated to form a columnar, nested, oblate, or the like structure. As long as the clamping assistance member 510 is made of a shape memory material, it can be received in the assistance arm accommodation chamber 250 of the pushing shaft 210 and pushed, and then passes through the opening 260 to return to the natural stretched state, contacts the lower surface of the leaflet and provides support for the leaflet.

Figure 22:
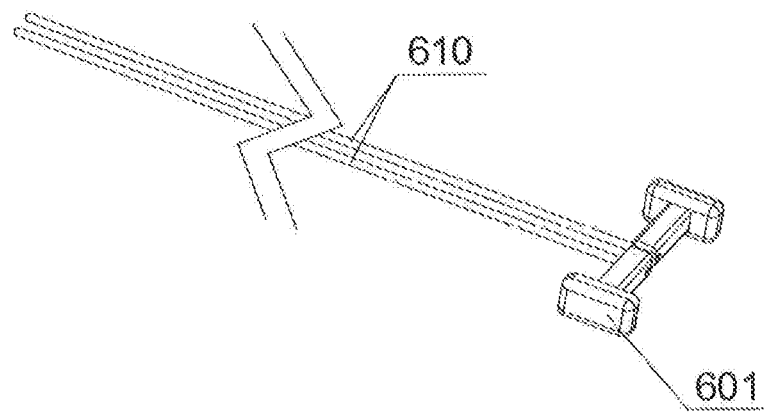
FIG. 22 is a structural schematic diagram of the detection device of the artificial chordae tendineae implantation system according to the first implementation manner of the first embodiment.
Figure 23:
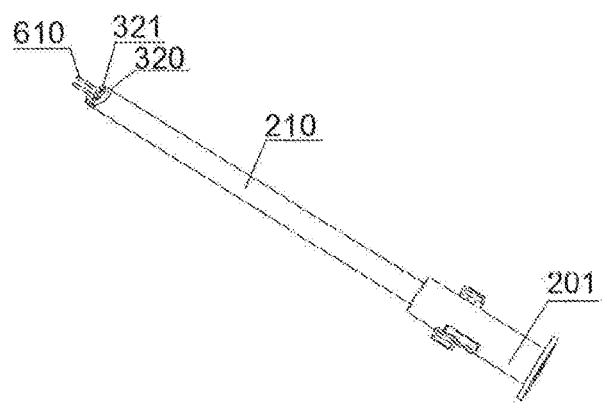
FIG. 23 is a structural schematic diagram of the detection device insertedly mounted within the pushing shaft as shown in FIG. 22.

As shown in FIG. 22 to FIG. 23, the detection device 600 is used to detect whether the leaflet is clamped between the distal clamp 310 and the proximal clamp 320. The detection device 600 includes at least one probe 610. In this embodiment, the detection device 600 includes two probes 610, and the two probes 610 are arranged in parallel, and the distance between the two probes 610 and the clamping push rod 330 is substantially equal respectively.

The axial length of the probe 610 is particularly greater than the axial length of the pushing shaft 210. The probe 610 is movably insertedly mounted within the pushing shaft 210. To facilitate the operation, the proximal end of the probe 610 is connected to the detection handle 601. The detection handle 601 and the probe 610 can be integrally formed or in a connection, and the connection is selected from a detachable connection such as a threaded connection or a snap fitting connection, or a non-detachable connection such as welding or bonding. The clamping surface of the proximal clamp 320 is provided with a probe outlet 321, thereby facilitating the passing through of the distal end of the probe 610 from the probe outlet 321. The clamping surface of the distal clamp 310 is provided with a probe accommodation chamber 316 correspondly (as shown in FIG. 9) that is opposite to the probe outlet 321 and is used for receiving the distal end of the probe 610. When the clamping device 300 is closed, the distal end of the probe 610 passes through from the probe outlet 321 and is received in the probe accommodation chamber 316.

Figure 24:
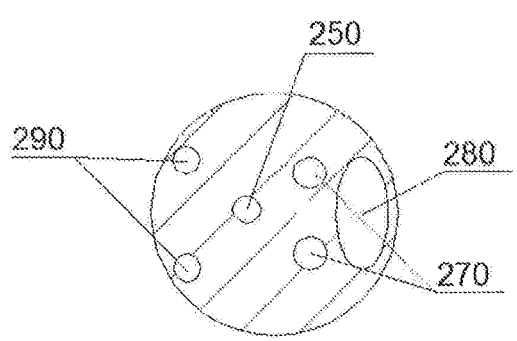
FIG. 24 is a radial cross-sectional view of the pushing shaft in the artificial chordae tendineae implantation system according to the first embodiment.

Referring to FIG. 24, the pushing shaft 210 is axially provided with a probe channel 270, a clamping push rod channel 280, and a puncture push rod channel 290. The clamping push rod 330 is insertedly mounted within the clamping push rod channel 280 of the pushing shaft 210, and the puncture push rod 420 is insertedly mounted within the puncture push rod channel 290 of the pushing shaft 210, so as to ensure that the axial directions of the clamping push rod 330 and the puncture push rod 420 are both parallel to the axial direction of the pushing shaft 210. The clamping push rod channel 280 is disposed on one side of the pushing shaft 210, and two puncture push rod channels 290 are disposed on the other side of the pushing shaft 210. The probe channel 270 is disposed between the clamping push rod channel 280 and the puncture push rod channel 290, and the distance between the probe channel 270 and the clamping push rod channel 280 is less than the distance between the probe channel 270 and the puncture push rod channel 290. It is understood that, when the pushing shaft 210 is also provided with an assistance arm accommodation chamber 250, the assistance arm accommodation chamber 250 is disposed between the clamping push rod channel 280 and the puncture push rod channel 290, and the probe channel 270 is disposed between the clamping push rod channel 280 and the assistance arm accommodation chamber 250, and the distance between the probe channel 270 and the clamping push rod channel 280 is less than the distance between the probe channel 270 and the puncture push rod channel 290.

When the clamping device 300 is closed, if the leaflet is clamped between the proximal clamp 320 and the distal clamp 310, and the leaflet edge is in contact with the clamping push rod 330, the distal end of the probe 610, after passing through from the clamping surface of the proximal clamp 320, will be stopped by the leaflet from moving further towards the distal end, thereby indicating that the clamping effect of the leaflet is good and the puncturing may be performed. In addition, when the distal end of the probe 610 is stopped by the leaflet and cannot enter into the probe accommodation chamber, it also indicates that the position between the leaflet edge and the chorda tendinea main body 110 is constant, thereby improving the therapeutic effect of artificial chordae tendineae implantation. As such, by using a probe in a mechanical structure, the clamping effect of the leaflet can be efficiently detected, with a simpler structure and convenient operations.

The probe 610 includes a probe main body having a certain length. The probe main body may be a solid or hollow structure. The cross section of the probe main body may be a regular circular or elliptical shape, a crescent shape, a semicircular shape, a polygonal shape, or the like, and particularly a circular shape. The probe main body can be made of a metal material, a polymer material, or a metal-polymer material. For example, the probe main body may be a solid rod-shaped or hollow tubular structure having a single-layer or multi-layer composite structure, or may be wound from a single wire or a plurality of wires.

The distal end of the probe main body has a hardness less than or equal to the hardness of the proximal end of the probe main body. Particularly, the distal end of the probe main body has a hardness that is less than the hardness of the proximal end of the probe main body. That is, the distal end of the probe main body particularly has flexibility or elasticity to avoid puncturing or damage of the leaflet, and the proximal end of the probe main body particularly has a structure of hardness or stiffness to provide support and push abilities.

The distal end and the proximal end of the probe main body may be integrally formed or may be separately processed then connected together by welding, bonding, socketing, threading, interference fit, or other common techniques in the field. That is, the support of the proximal end and the flexibility of the distal end of the probe main body may be achieved by using different materials to make the proximal end and the distal end of the probe main body respectively. It is understood that, in other embodiments, the whole rod body or tube body may be made of a softer material first, and then an outer tube having a higher hardness is used as a reinforcing tube to be sleeved on the outer surface of the proximal end of the rod body or the tube body to improve the support of the proximal end of the probe main body; a heat-shrinkable tube may also be used as a reinforcing tube to wrap around the softer proximal end of the rod body or the tube body, and then the heat-shrinkable tube is heated to shrink and wrap around the outer surface of the proximal end to improve the support of the proximal end of the probe main body. It is also understood that, for a rod body or a tube body wound from a single wire or a plurality of wires, a thermoplastic elastomer such as Pebax or nylon may be wrapped around the outer surface of the proximal end of the rod body or the tube body, and then the thermoplastic elastomer is heated to melt and wrap the outer surface meanwhile infiltrating into the gap between multiple or single wire, thereby improving the support of the proximal end of the probe main body.

It can be understood that, in other embodiments, the probe 610 may also be provided with a probing head disposed at the distal end of the probe main body, and the probing head and the probe main body are integrally formed or in a fixed connection. The fixed connection is a detachable connection or a non-detachable connection. The probing head at the distal end of the probe 610 has particularly a smooth outer surface structure to avoid damage to the leaflet. For example, a smooth round head can be formed by laser spot welding without defects such as burrs, edges, corners and the like. The probing head may be a solid or hollow structure, but for the ease of pushing, the shape of the probing head is selected from at least one of a cone shape, a table shape, a column shape, a sphere shape, or a hemisphere shape. The probing head can be made of a metal material, a polymer material or a metal-polymer material.

Figure 25:
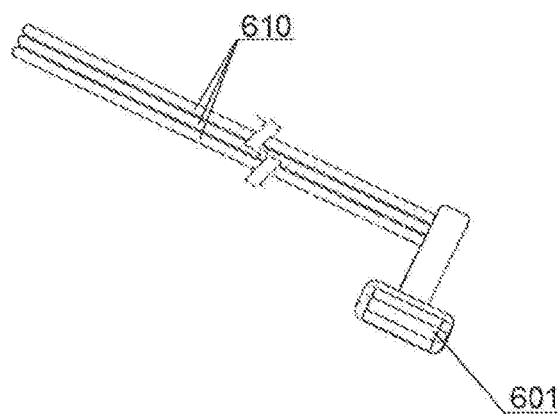
FIG. 25 is a structural schematic diagram of the detection device according to the second implementation manner.

It can also be understood that, in other embodiments, the detection device 600 may include only one probe 610, and may also include a plurality of probes 610 (three probes as shown in FIG. 25). The plurality of probes 610 may be commonly insertedly mounted within an inner chamber of the pushing shaft 210. That is, the pushing shaft 210 is provided with only one probe channel 270, or may be separately insertedly mounted in different inner chambers of the pushing shaft 210, i.e., the pushing shaft 210 is provided with a plurality of probe channels 270.

Figure 26:
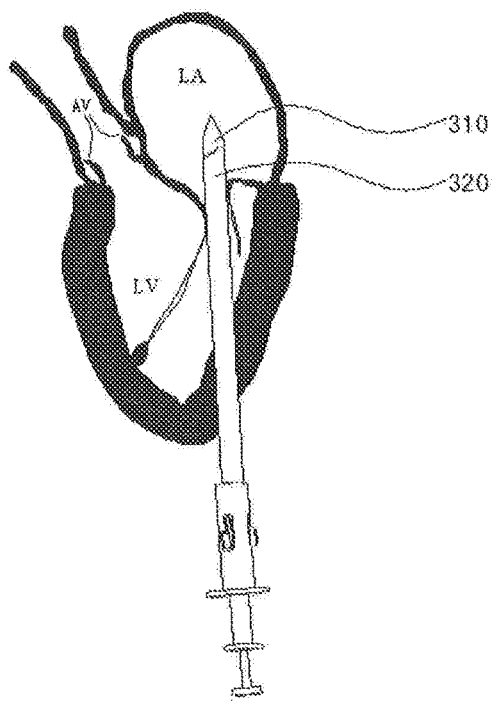
FIG. 26 to FIG. 36 are schematic diagrams of the process of using the artificial chordae tendineae implantation system according to the first embodiment to implant artificial chordae tendineae.

The following is an example of chordae tendineae implantation to a clamped posterior leaflet of a mitral valve, for illustrating the implementation process of the artificial chordae tendineae implantation system:

At first step: referring to FIG. 26, the artificial chordae tendineae implantation system is pushed into the left ventricle (LV), and the artificial chordae tendineae implantation system is pushed further till the distal clamp 310 and the proximal clamp 320 are both located inside the left atrium (LA).

Figure 27:
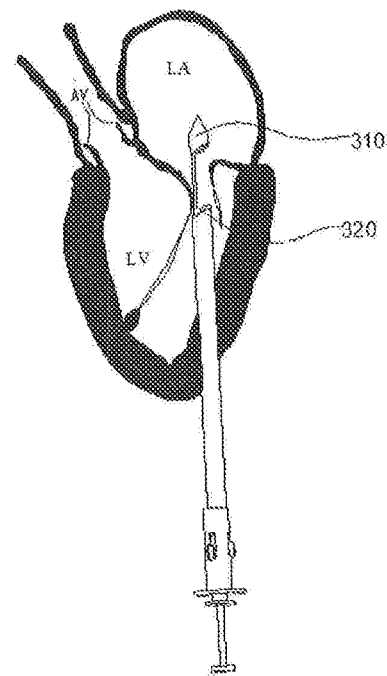

At second step: referring to FIG. 27, the pushing shaft 210 is retracted towards the proximal end or the clamping push rod 330 is pushed towards the distal end, causing the proximal clamp 320 to be separated from the distal clamp 310, at this time a leaflet accommodation space is formed between the proximal clamp 320 and the distal clamp 310.

Figure 28:
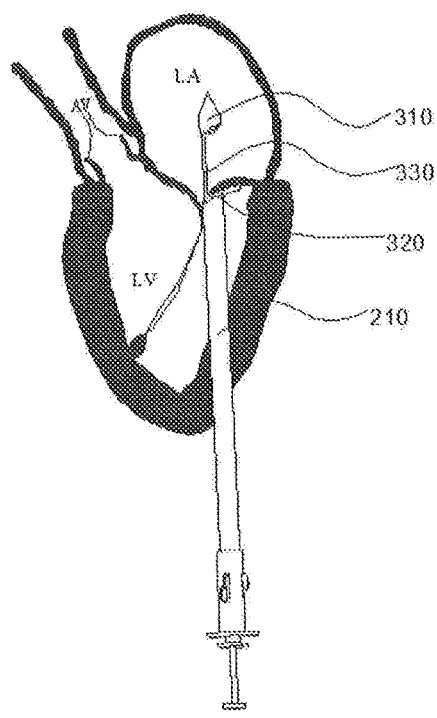

At third step: referring to FIG. 28, the fourth handle 501 is pushed towards the distal end, and the fourth handle 501 drives the clamping assistance arm 520 to push the clamping assistance member 510 to pass through from the opening 260, at this time the clamping assistance member 510 supports the lower surface of the leaflet to cooperatively stabilize the flapping leaflet; keeping the relative positions of the first handle 201, the second handle 301, and the fourth handle 501 unchanged, moving the entire artificial chordae tendineae implantation system towards the proximal end slowly, till the leaflet enters into the leaflet accommodation space formed between the proximal clamp 320 and the distal clamp 310, and the clamping assistance member 510 may provide certain support for the leaflet.

Figure 29:
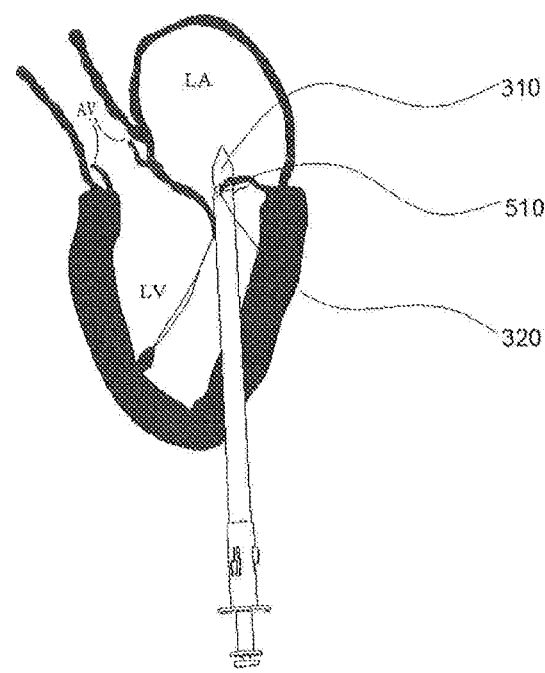
Figure 30:
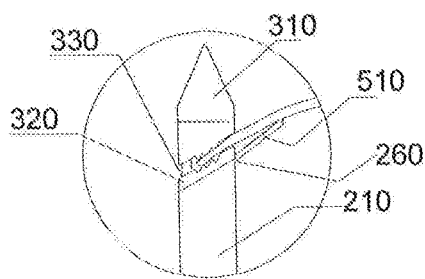

At fourth step: referring to FIG. 29 and FIG. 30, moving the distal end of the artificial chordae tendineae implantation system slightly, till the leaflet edge contacts the clamping push rod 330, at this time retracting the second handle 301 towards the proximal end, driving the distal clamp 310 to move towards the proximal clamp 320 till the leaflet is clamped.

Figure 31A:
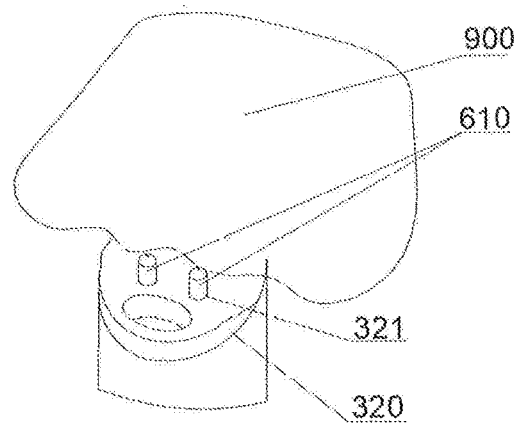
Figure 31B:
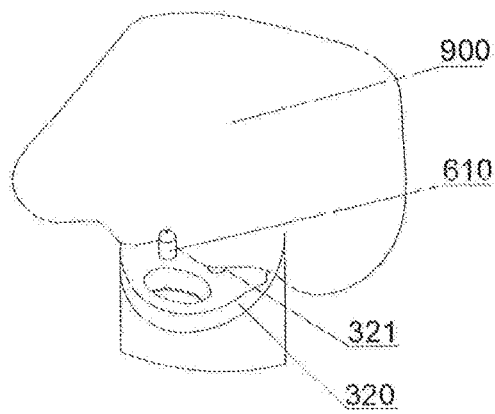
Figure 31C:
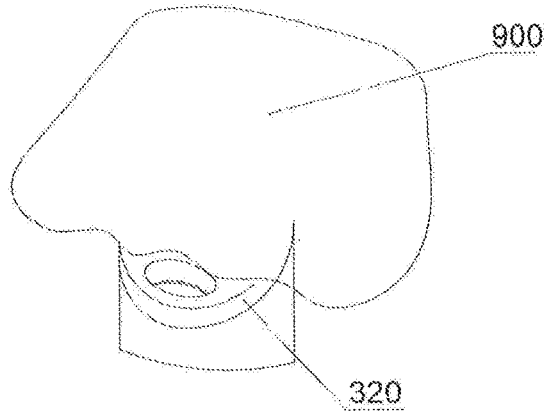

At fifth step: keeping the position of the first handle 201 unchanged, driving the detection handle 601 towards the distal end, driving the probe 610 to move towards the distal end along the axial direction of the pushing shaft 210; as shown in FIG. 31a or FIG. 31b, if the clamping state of the leaflet 900 is poor, i.e., the leaflet 900 does not fully cover the probe outlet 321 on the clamping surface of the proximal clamp 320, the distal end of the probe 610 may pass through the probe outlet 321 and then enters into the probe accommodation chamber 316 of the distal clamp 310, the second step to the fourth step must be repeated to clamp the leaflet 900 again; as shown in FIG. 31c, if the clamping state of the leaflet 900 is good, i.e., the leaflet 900 fully covers the probe outlet 321 on the clamping surface of the proximal clamp 320, the distal end of the probe 610 cannot pass through the probe outlet 321 and then enter into the probe accommodation chamber 316 of the distal clamp 310, the following operations may proceed.

Figure 32:
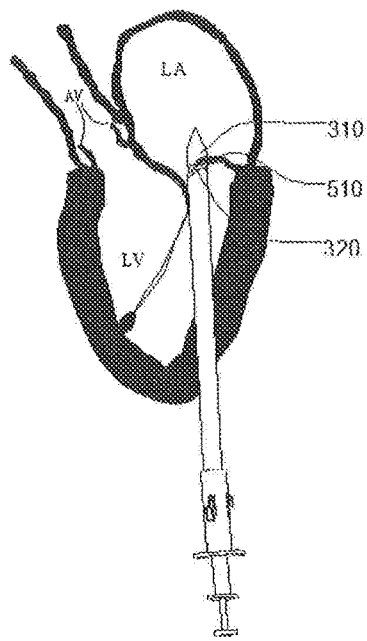
Figure 33A:
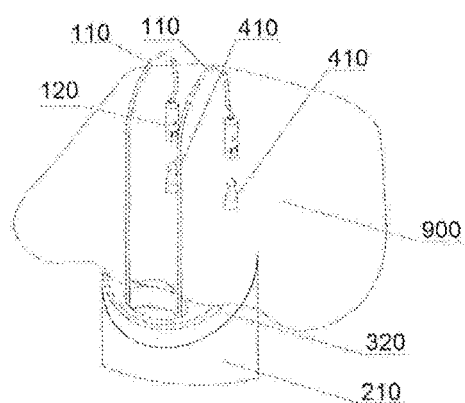
Figure 33B:
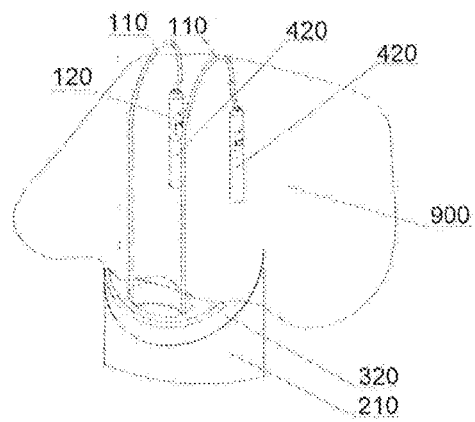

At sixth step: referring to FIG. 32, the third handle 401 is pushed towards the distal end, driving the puncture needle 410 to move towards the distal end, till the puncture needle 410 pass through the leaflet, as shown in FIG. 33a, and forms a connection with the fixing member 120 of the artificial chorda tendinea 100 as shown in FIG. 33b.

Figure 34:
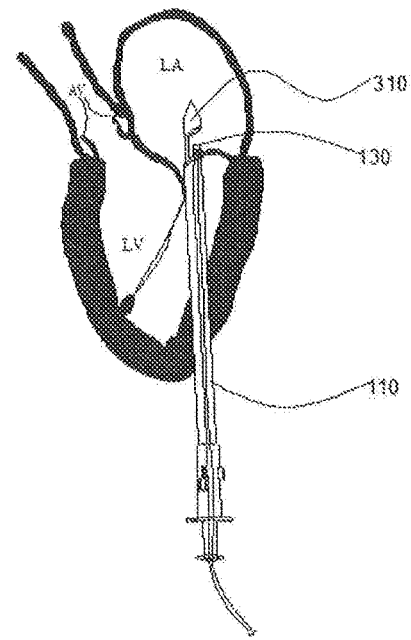
Figure 35:
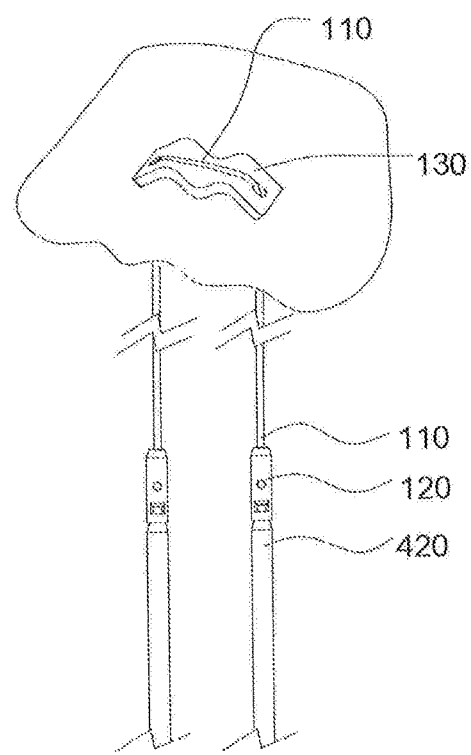

At seventh step: referring to FIG. 34, the third handle 401 is retracted, and makes the puncture needle 410 to drive the fixing member 120 of the artificial chorda tendinea 100, the chorda tendinea main body 110 connected with the fixing member 120 to successively pass through the leaflet, the anti-slip member 130 is also pulled from the clamping surface of the distal clamp 310, the fitting surface of the anti-slip member 130 (i.e., the lower surface) fits the upper surface of the leaflet, meanwhile part of the chorda tendinea main body 110 presses the upper surface of the anti-slip member 130 to make the anti-slip member 130 fit the leaflet (as shown in FIG. 35). At this time, the point contact between the artificial chorda tendinea 100 and the leaflet is converted into a face contact between the anti-slip member 130 and the leaflet, thereby efficiently reducing the risk of tearing the leaflet.

Figure 36:
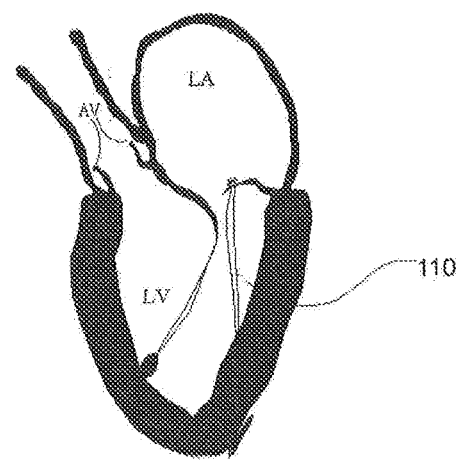

At eighth step: continuously retracting the third handle 401 till the fixing member 120 is retracted from the proximal end of the pushing shaft 210, and then the fourth handle 501 is retracted, to move the clamping assistance member 510 to retract to the assistance arm accommodation chamber 250, retracting the entire artificial chordae tendineae implantation system, and adjusting the length of the chorda tendinea main body 110 remaining in the heart, fixing both ends of the chorda tendinea main body 110 to the ventricular wall, completing the artificial chordae tendineae implantation (as shown in FIG. 36).

In the fourth step, if the operator finds out that the clamp is not efficiently clamped, at this time the relative position of the distal clamp 310 and the proximal clamp 320 may be fine adjusted to create a certain distance between the distal clamp 310 and the proximal clamp 320, then adjusting the relative position between the clamping push rod 330 and the leaflet, again operating the clamping device 300 to clamp the leaflet, then performing the surgical operation at the fifth step. During the adjustment process, because the clamping assistance device 500 below the leaflet has a certain supporting function for the leaflet, it may prevent the leaflet from slipping away from the clamping device 300.

The Second Embodiment

The artificial chordae tendineae implantation system having a detection device according to the second embodiment has basically the same structure as the artificial chordae tendineae implantation system according to the first embodiment, and the differences are: in the artificial chordae tendineae implantation system of the second embodiment, the two probes 610 of the detection device 600 are disposed in parallel and the distal ends of the two probes 610 are connected.

Figure 37:
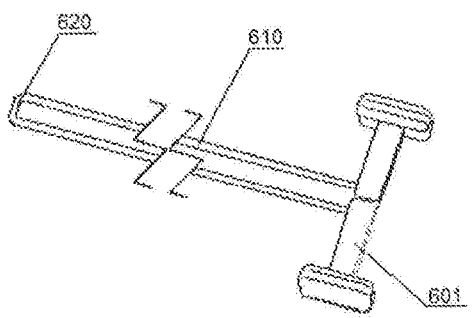
FIG. 37 is a structural schematic diagram of the detection device of the artificial chordae tendineae implantation system according to the second embodiment.
Figure 38:
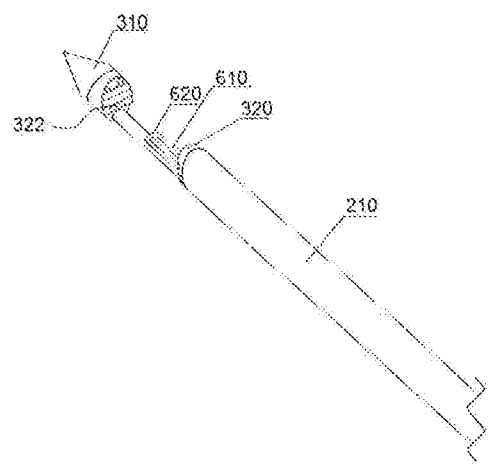
FIG. 38 is a structural schematic diagram of the detection device and the clamping device insertedly mounted within the pushing shaft according to the second embodiment.
Figure 39:
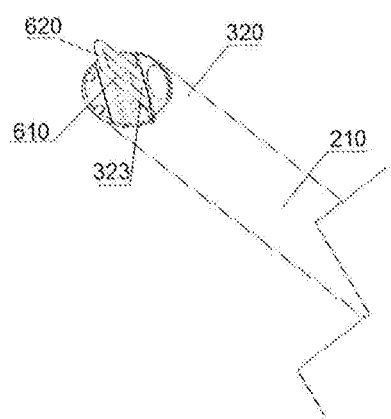
FIG. 39 is a structural schematic diagram of the distal end of the detection device passing through the clamping surface of the proximal clamp according to the second embodiment.

Referring to FIG. 37 to FIG. 39, the distal end of the probe 610 has a certain elasticity/toughness, and is connected together by the connecting rod 620. When the detection handle 601 is retracted, the connecting rod 620 is disposed on the clamping surface of the proximal clamp 320. The clamping surface of the proximal clamp 320 is particularly configured for receiving the recess 323 of the connecting rod 620, and the recess 323 is connected with the probe channel 270. Correspondingly, the clamping surface of the distal clamp 310 is provided with a connecting rod accommodation indentation 322 for receiving the connecting rod 620, and the connecting rod accommodation indentation 322 is connected respectively with two probe accommodation chambers 316. When the detection handle 601 of the detection device 600 is pushed towards the distal end, the distal ends of the two probes 610 and the connecting rod 620 both pass through the proximal clamp 320, and enter into the connecting rod accommodation indentation 322 of the distal clamp 310 and the probe accommodation chamber 316; when the detection handle 601 is retraced towards the proximal end, the distal ends of the two probes 610 and the connecting rod 620 are retracted from the distal clamp 310, the distal ends of the probes 610 are received in the probe channel 270 of the pushing shaft 210, and the connecting rod 620 is received in the clamping surface of the proximal clamp 320 or the clamping surface of the recess 323.

Figure 40:
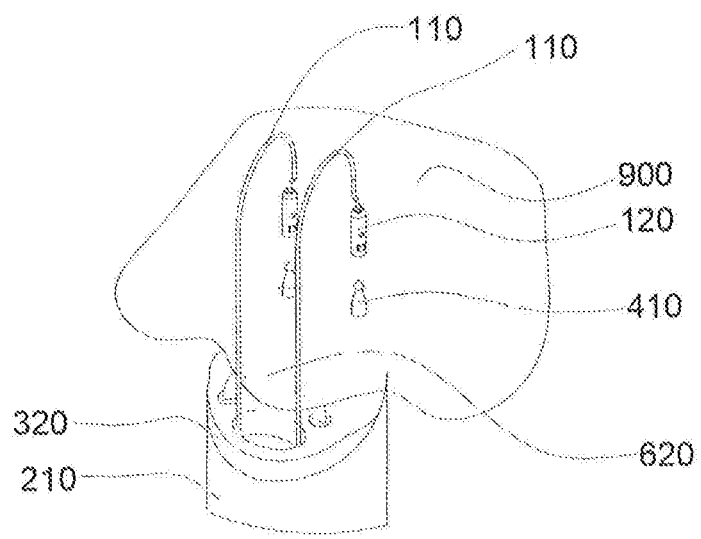
FIG. 40 is a schematic diagram of the process of using the artificial chordae tendineae implantation system according to the second embodiment to implant chordae tendineae.

In this embodiment, because the contact area between the distal end of the detection device 600 and the leaflet is increased, making it especially suitable for detecting irregular leaflet shapes. For example, as shown in FIG. 40, due to the irregular shape of the edge of the leaflet, even when the leaflet is efficiently clamped by the clamping device 300, the leaflet may just not cover the probe outlet 321 of the proximal clamp 320. But the distal ends of the two probes 610 of this embodiment are connected together by the connecting rod 620, increasing the contact area between the distal end of the detection device 600 and the leaflet, allowing the detection of the clamping of the leaflet, further instructing the operator to perform leaflet puncture to implant artificial chordae tendineae.

The method of usage of the artificial chordae tendineae implantation system of this embodiment is basically the same as the method of usage of the artificial chordae tendineae implantation system according to the first embodiment, and will not be repeated herein.

The Third Embodiment

The artificial chordae tendineae implantation system having a detection device according to the third embodiment has basically the same structure as the artificial chordae tendineae implantation system according to the first embodiment, and the differences are: in the artificial chordae tendineae implantation system of the third embodiment, the probe 610 of the detection device 600 is movably inserted mounted within the clamping push rod 330.

Figure 41:
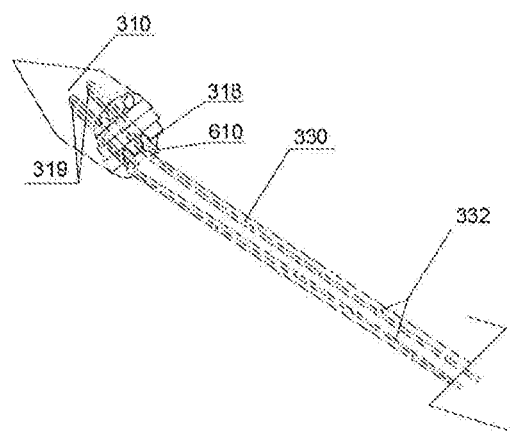
FIG. 41 is a structural schematic diagram of the detection device, the clamping push rod, and the distal clamp of the artificial chordae tendineae implantation system having the detection device according to the third embodiment of the present disclosure.
Figure 42:
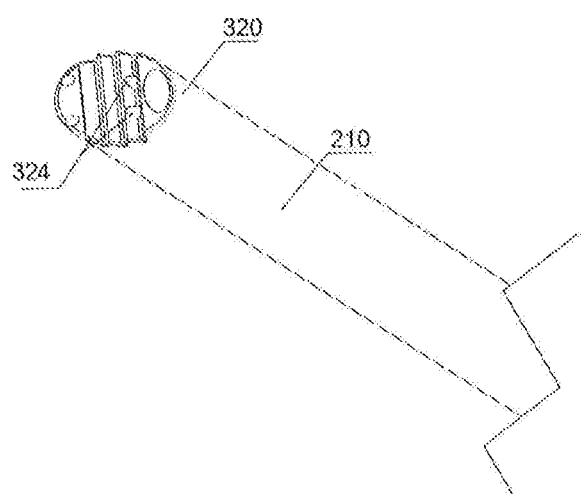
FIG. 42 is a structural schematic diagram of the pushing shaft and the proximal clamp according to the third embodiment.

Specifically, referring to FIG. 41 and FIG. 42, the probe 610 is insertedly mounted within the clamping push rod 330, the clamping push rod 330 is inserted mounted within the pushing shaft 210, i.e., the probe 610 is also located within the inner chamber of the clamping push rod 330. The distal end of the probe 610 is bent and then bent towards the proximal end, and is received in the distal clamp 310. The clamping surface of the distal clamp 310 is provided with a probe outlet 318, and the clamping surface of the corresponding proximal clamp 320 is provided with a probe accommodation chamber 324 corresponding to the probe outlet 318.

A bent probe curve 319 is disposed in the distal clamp 310, and one end of the probe curve 319 is connected with the probe channel 332 of the clamping push rod 330, and the other end is through connected to the probe outlet 318 of the clamping surface of the distal clamp 310. The probe 610 passes through the probe channel 332 of the clamping push rod 330 and the probe curve 319. The distal end of the probe 610 has a certain flexibility and toughness, and maintains a straight state in a natural state, and may be pressed to bent and move axially in the curve. It is understood that, in other embodiments, there is no need to separately provide a probe channel 322, and the inner chamber of the clamping push rod 330 may be used as the probe channel 332.

The implementation process of the detection device 600 of the artificial chordae tendineae implantation system of this embodiment is: after the leaflet is clamped, by moving the detection handle 601, the probe 610 is driven to move axially, the distal end of the probe 610 is bent when passing the bent probe curve 319 in response to the shape of the probe curve 319, and continues to advance, if the distal end of the probe 610 passes through the probe outlet 318 of the clamping surface of the distal clamp 310 and enters into the probe accommodation chamber 324 of the clamping surface of the proximal clamp 320, it indicates that the clamping effect is poor and requires adjusting the clamping position to clamp again; if the distal end of the probe 610 after driven by the detection handle 601 cannot enter into the probe accommodation chamber 324 from the probe outlet 318, it indicates that the leaflet has completely or almost completely fill the leaflet accommodation space between the proximal clamp 320 and the distal clamp 310, the clamping effect of the leaflet is good, and the leaflet puncture may be performed to implant artificial chordae tendineae.

Overall, the artificial chordae tendineae implantation system having a detection device of the present disclosure, uses a probe in mechanical form as the detection device, making the structure of the device simple, reducing the surgical risk, and having a low manufacturing cost, reducing the economic burden of a patient.

The foregoing implementations are merely specific embodiments of the present disclosure, and are not intended to limit the protection scope of the present disclosure. It should be noted that any variation or replacement readily figured out by persons skilled in the art within the technical scope disclosed in the present disclosure shall all fall into the protection scope of the present disclosure. Therefore, the protection scope of the present disclosure shall be subject to the protection scope of the claims.

What is claimed is:

1. An artificial chordae tendineae implantation system, comprising a clamping device, a puncture device, a pushing device, and a detection device, the pushing device comprises a pushing shaft;

the clamping device comprises a clamping push rod that receives at least an artificial chorda tendinea, a distal clamp and a proximal clamp for cooperatively clamping a leaflet;

the distal clamp is disposed at a distal end of the clamping push rod;

the proximal clamp is disposed at a distal end of the pushing shaft;

the puncture device and the clamping push rod are movably insertedly mounted within the pushing shaft respectively;

the detection device comprises at least a probe, the probe is movably insertedly mounted within the pushing shaft;

a probe outlet is provided at one of a clamping surface of the proximal clamp and a clamping surface of the distal clamp, and a probe accommodation chamber corresponding to the probe outlet is provided at the other one of the clamping surface of the proximal clamp and the clamping surface of the distal clamp;

when the distal clamp closes with the proximal clamp, a distal end of the probe protrudes from the probe outlet and is received in the probe accommodation chamber.

2. The artificial chordae tendineae implantation system according to claim 1, wherein an axial length of the probe is longer than an axial length of the pushing shaft.

3. The artificial chordae tendineae implantation system according to claim 1, wherein the probe comprises a probe main body having a length, the probe main body being solid or hollow.

4. The artificial chordae tendineae implantation system according to claim 3, wherein a hardness of a distal end of the probe main body is smaller than or equal to a hardness of a proximal end of the probe main body.

5. The artificial chordae tendineae implantation system according to claim 3, wherein the probe further comprises a probing head disposed at a distal end of the probe main body, the probe being integrally formed or in a connection with the probe main body, the connection being detachable or non-detachable.

6. The artificial chordae tendineae implantation system according to claim 5, wherein an outer surface of the probe is smooth, the probe is solid or hollow, a shape of the probe is selected from at least one of a cone shape, a table shape, a column shape, a sphere shape, or a hemisphere shape.

7. The artificial chordae tendineae implantation system according to claim 1, wherein the number of the probes is two.

8. The artificial chordae tendineae implantation system according to claim 7, wherein the two probes are disposed in parallel, and the distal ends of the two probes are connected.

9. The artificial chordae tendineae implantation system according to claim 1, wherein the detection device further comprises a detection handle disposed at a proximal end of the probe, the detection handle being integrally formed or in a connection with the probe, the connection being detachable or non-detachable.

10. The artificial chordae tendineae implantation system according to claim 1, wherein the pushing shaft is provided with a probe channel, a clamping push rod channel, and a puncture push rod channel in an axial direction, the probe channel being disposed between the clamping push rod channel and the puncture push rod channel, a distance between the probe channel and the clamping push rod channel being smaller than a distance between the probe channel and the puncture push rod channel.

11. The artificial chordae tendineae implantation system according to claim 1, wherein the artificial chorda tendinea comprises a flexible chorda tendinea main body, the chorda tendinea main body comprises a first end and a second end respectively, the first end and/or the second end are connected to a fixing member, the fixing member is configured for a detachable or non-detachable connection with the puncture device.

12. The artificial chordae tendineae implantation system according to claim 11, wherein the chorda tendinea main body is received in the clamping push rod and the distal clamp, the fixing member is received in the distal clamp, a proximal end of the fixing member corresponds to a distal end of the puncture device.

13. The artificial chordae tendineae implantation system according to claim 12, wherein the clamping push rod is provided with an artificial chorda tendinea channel in an axial direction, the distal clamp is provided with an artificial chorda tendinea accommodation chamber, the artificial chorda tendinea accommodation chamber is in a through connection with the clamping surface of the distal clamp, the artificial chorda tendinea channel is connected with the artificial chorda tendinea accommodation chamber, the chorda tendinea main body is received in the artificial chorda tendinea channel and the artificial chorda tendinea accommodation chamber.

14. The artificial chordae tendineae implantation system according to claim 13, wherein the clamping surface of the distal clamp is provided with a fixing chamber for receiving the fixing member, the fixing chamber is axially connected with the artificial chorda tendinea accommodation chamber.

15. The artificial chordae tendineae implantation system according to claim 14, wherein a shape of the fixing chamber corresponds to a shape of the fixing member, a diameter of an inscribed circle of the fixing chamber is larger than a diameter of a circumcircle of the artificial chorda tendinea accommodation chamber.

16. The artificial chordae tendineae implantation system according to claim 1, wherein the artificial chorda tendinea comprises a flexible chorda tendinea main body, the chorda tendinea main body comprises a first end and a second end respectively; wherein the chorda tendinea main body is sleeved with an anti-slip member, the anti-slip member is provided with a fitting surface that fits the leaflet, the anti-slip member slides in an axial direction of the chorda tendinea main body.

17. The artificial chordae tendineae implantation system according to claim 16, wherein the anti-slip member is provided with a through hole, the chorda tendinea main body passes through the through hole;

or the anti-slip member is provided with at least two through holes, a first end and a second end of the chorda tendinea main body pass through different through holes respectively;

or the anti-slip member is provided with at least two through holes, at least two chorda tendinea main bodies pass through different through holes respectively.

18. The artificial chordae tendineae implantation system according to claim 16, wherein the clamping surface of the distal clamp is provided with an accommodation indentation for receiving the anti-slip member, the accommodation indentation is radially connected with the artificial chorda tendinea accommodation chamber, the accommodation indentation is radially connected with the fixing chamber.

19. The artificial chordae tendineae implantation system according to claim 1, further comprising a clamping assistance device; the clamping assistance device comprises at least a clamping assistance arm that is movably insertedly mounted within the pushing shaft and a clamping assistance member that is disposed at a distal end of the clamping assistance arm; the clamping assistance member is made of a flexible and/or elastic material; the clamping assistance arm pushes the clamping assistance member that is connected with the clamping assistance arm to pass through from the distal end of the pushing shaft or the distal end of the clamping device; the clamping assistance member cooperates with the clamping device to clamp the leaflet.

20. The artificial chordae tendineae implantation system according to claim 19, wherein the pushing shaft is provided with an assistance arm accommodation chamber in an axial direction, an angle between an axis of a distal end of the assistance arm accommodation chamber and an axis of the pushing shaft is 120° to 150°.

21. The artificial chordae tendineae implantation system according to claim 19, wherein the clamping assistance member is at least partially made of a material opaque to X-rays.

* * * * *